(12) United States Patent
Kimura

(10) Patent No.: US 7,833,397 B2
(45) Date of Patent: Nov. 16, 2010

(54) AMINO-ACID BIOSENSOR, FISCHER-RATIO BIOSENSOR AND HEALTH INFORMATION MANAGEMENT SYSTEM

(75) Inventor: Eiichiro Kimura, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/498,982

(22) Filed: Aug. 4, 2006

(65) Prior Publication Data

US 2007/0031913 A1 Feb. 8, 2007

Related U.S. Application Data

(63) Continuation of application No. PCT/JP2005/001781, filed on Feb. 7, 2005.

(30) Foreign Application Priority Data

Feb. 6, 2004 (JP) ............................ 2004-030453

(51) Int. Cl.
*G01N 27/26* (2006.01)
*C12Q 1/32* (2006.01)
(52) U.S. Cl. .................... 204/403.04; 435/26
(58) Field of Classification Search .............. 435/25, 435/26; 205/777.5, 787; 204/403.01, 403.04
See application file for complete search history.

(56) References Cited

U.S. PATENT DOCUMENTS

| | | |
|---|---|---|
| 5,283,181 A | 2/1994 | Uchida et al. |
| 6,468,416 B1 * | 10/2002 | Nakamura et al. ....... 205/777.5 |
| 6,720,164 B1 * | 4/2004 | Shinozuka et al. ............ 435/26 |

FOREIGN PATENT DOCUMENTS

EP 0 264 815 A1 10/1987

(Continued)

OTHER PUBLICATIONS

Lobo, MJ, et al. "Amperometric Biosensors Based on NAD(P)-Dependent Dehydrogenase Enzymes", Electrolysis, vol. 9, No. 3, Feb. 1997, pp. 191-202.*
Albery, W. J., et al., "Amperometric enzyme electrodes" Philosophical Transactions of the Royal Society of London, vol. B 316, Aug. 28, 1987, p. 107-119.*

*Primary Examiner*—Nam X Nguyen
*Assistant Examiner*—J. Christopher Ball
(74) *Attorney, Agent, or Firm*—Foley & Lardner LLP

(57) ABSTRACT

Disclosed is a biosensor capable of measuring a total concentration of plural types of amino acids. An amino-acid biosensor (200) for measuring a total concentration of a plurality of specific amino acids, comprises a measuring electrode (202) which includes as components a mediator and an enzyme which selectively act on the plurality of specific amino acids each serving as a substrate, and a counter electrode (203). The enzyme has a substrate affinity to each of the plurality of specific amino acids. The enzyme is operable to catalyze a reaction in each of the plurality of specific amino acids as a substrate so as to form a reaction product, and the mediator is operable, during amino-acid concentration measurement, to carry electrons between the reaction product and the measuring electrode. The amino-acid biosensor is designed to apply a voltage between the measuring electrode and the counter electrode during the measurement in such a manner that, in an analytical curve representing a relationship between an applied voltage and a current value for each of the plurality of specific amino acids, the applied voltage includes a voltage allowing the variety of the current values for the amino acids at the same applied voltage to fall within a given range.

6 Claims, 14 Drawing Sheets

FOREIGN PATENT DOCUMENTS

| | | |
|---|---|---|
| JP | 63-226299 A | 9/1988 |
| JP | 4-125461 A | 4/1992 |
| JP | 2000-035413 A | 2/2000 |
| JP | 2003-194769 A | 7/2003 |
| JP | 2003-310560 A | 11/2003 |
| WO | WO 00/57166 A1 | 9/2000 |
| WO | WO 02/18627 A1 | 3/2002 |

* cited by examiner

FIG. 13

HEALTH INFORMATION MANAGEMENT SYSTEM
MEMBERSHIP REGISTRATION SCREEN

NAME [          ]

SEXUALITY ☐ MALE        ☐ FEMALE

BIRTH DATA [    ] Y [    ] M [    ] D

ADDRESS [              ]

TEL [         ]

[ REGISTRATION ]   [ RESET ]

FIG. 14

HEALTH INFORMATION MANAGEMENT SYSTEM
MEASURED-VALUE OUTPUT SCREEN

EXAMINATION RESULT OF MR./MS.☐☐☐

EXAM. DATE [    ] Y [    ] M [    ] D

BCAA CONCENTRATION [        ]

FISCHER RATIO [        ]

[ NEXT ]   [ RETURN ]

AMINO-ACID BIOSENSOR, FISCHER-RATIO BIOSENSOR AND HEALTH INFORMATION MANAGEMENT SYSTEM

TECHNICAL FIELD

The present invention relates to an amino-acid biosensor, and more specifically to an amino-acid biosensor capable of measuring a health index, such as a Fischer ratio, by a single measurement operation. The present invention also relates to a health information management system, and more specifically to a health information management system for managing/evaluating a health index, such as a Fischer ratio, measured using the amino-acid biosensor by an individual, for example, at home.

BACKGROUND ART

In connection with recent health-conscious trend, there is a growing societal need for measuring an index representing a health condition, i.e., a health index, as an objective numerical value. As to comprehensive biological information, such as body weight, body fat percentage and blood pressure, an apparatus for measuring such information and converting the detected information to electrical information has already been put into practical use. In contrast, an apparatus for directly measuring a numerical value of each biological component has not yet been really put into practical use. In particular, there is no practical apparatus for measuring a concentration of plural types of amino acids in blood or the like, in a simplified manner.

It is known that some amino acids can be used as a health index, and particularly a concentration of branched-chain amino acids (leucine, isoleucine and valine), or a concentration of aromatic amino acids (phenylalanine and tyrosine), reflects a health condition of a liver. Thus, a health index calculated from a concentration of branched-chain amino acids and a concentration of aromatic amino acids is also known as one item of a clinical examination. Specifically, a molar ratio (BCAAs/AAAs) of branched-chain amino acids (BCAAs) to aromatic amino acids (AAAs), so-called "Fischer ratio", and a molar ratio (BCAAs/Y) of branched-chain amino acids (BCAAs) to tyrosine (Y), so-called "BTR value" as a simpler value than the Fischer ratio, are used as an index representing a liver condition. It is known that a concentration of the branched-chain amino acids (BCAAs) consisting of leucine, valine and isoleucine becomes lower in a cirrhotic patient with advanced liver fibrosis. It is also known that a concentration of the aromatic amino acids (AAAs) consisting of phenylalanine and tyrosine becomes higher in a cirrhotic patient. That is, along with deterioration in liver function, each of the Fischer ratio and the BTR value will become smaller. Thus, each of the Fischer ratio and the BTR value can be used as a health index reflecting a liver condition. A concentration of the branched-chain amino acids is also used as a health index by itself.

While a method using a liquid chromatography process and a sensitivity enhancing technique based on an amino-acid marker in combination is widely used for measuring an amino-acid concentration, the measuring method involves complicated operations, such as preparation of samples, and requires taking a long time for measurement. Further, a biosensor designed to electrochemically detect an enzymatic reaction in an amino acid so as to measure an amino-acid concentration has been increasingly used as a method for quantifying an amino acid simply and quickly even though the applicable amino acid is limited to only several specific types. In most cases, a dehydrogenase is used as the enzyme, and it is necessary to additionally use a coenzyme. As to the conventional measurement of an amino-acid concentration using the biosensor based on an enzymatic reaction involving a dehydrogenase and a coenzyme, there has been known a technique of electrochemically measuring each of amino acids, such as L-leucine, and substances other than amino acids, such as D-glucose, L-lactic acid, ethanol and cholesterol, independently, using a biosensor (see, for example, the following Patent Publication 1). This technique is intended to provide a biosensor capable of electrochemically quantifying a substrate concentration with a high degree of accuracy and within a short time in a simplified manner, and being readily produced at low cost. Specifically, in a biosensor which comprises an electrode system made of an electrically conductive material and formed on an insulating support, and an absorbent carrier containing at least a dehydrogenase, a coenzyme and an electron mediator, as a reaction reagent, and disposed in an electrode reaction region, the absorbent carrier serves as a reaction layer for both an enzymatic reaction between the sample and the reaction reagent and an electrode reaction between the electrode mediator and an electrode surface. Further, as to the biosensor using a dehydrogenase and a coenzyme, there has been known a technique of quantifying each substrate of various samples quickly and in a simplified manner without the need for a complicated pretreatment, by a biosensor using a reaction reagent comprising an electron mediator and a tetrazolium salt (see, for example, the following Patent Publication 2). However, even the above techniques cannot simultaneously measure a concentration of plural types of amino acids.

[Patent Publication 1] Japanese Patent Laid-Open Publication No. 2000-35413

[Patent Publication 2] Pamphlet of PCT Publication WO 00/57166

DISCLOSURE OF THE INVENTION

While there are various indexes based on information about biological components, the present invention primarily covers an index based on information about amino acids. In particular, the present invention covers a concentration of branched-chain amino acids which is known for having relevance to a health condition, and a health index, such as a Fischer ratio or a BTR value, which is derived from amino-acid concentrations. There is a diagnostic kit for measuring amino acids to determine a health index, such as a Fischer ratio. Such diagnostic kit is required to use an analytical instrument, such as a calorimeter, in addition to a diagnostic reagent, and therefore a user is typically obligated to transfer a biological sample, such as blood, to a testing agency so as to perform the measurement. That is, a user cannot perform the measurement for himself/herself to know his/her physical condition/health condition on site.

An amino-acid concentration can be measured through a method using a liquid chromatography process in combination with an amino-acid marker based on a ninhydrin reaction or the like, or through a method of quantifying a reaction product resulting from an enzymatic reaction in an amino-acid substrate, by absorptiometry. However, these methods require a pretreatment, such as diluting and isolation of a sample, and large-scale equipment. Thus, it is difficult to quickly perform the measurement in a simplified manner. Moreover, in a process of calculating a total concentration of branched-chain amino acids using a commercially-available amino-acid analyzer, it is necessary to measure each concentration of leucine, isoleucine and valine independently, and then sum up the respective measured concentrations. There has also been known a biosensor capable of measuring an amino acid or the like in a simplified manner. This conventional biosensor can measure, only for several specific types of amino acids, each of said amino acids independently. However, under the condition that a plurality of specific amino acids capable of serving as a substrate for an enzyme used in the biosensor simultaneously exist, as in the measurement of a total concentration of branched-chain amino acids, it is impossible for the conventional biosensor to measure each of the amino acids independently and a total concentration of the plurality of specific amino acids. As above, there has been no biosensor capable of measuring a total concentration of branched-chain amino acids by itself. Further, in order to obtain a health index to be derived from a plurality of amino-acid concentrations, the conventional biosensors are essentially required to measure each of amino-acid concentrations relating to the health index and then sum up them on a calculation basis. That is, there has been no biosensor capable of measuring a health index by a single measurement operation. Furthermore, the conventional biosensors are not designed to allow a user to personally measure an amino acid-based health index in a simplified manner, and therefore there has been no health information management system utilizing such a health index. In view of the above problems, it is an object of the present invention to provide a biosensor and a health information management system, capable of measuring a total concentration of a plurality of specific amino acids by a single operation.

The above object is achieved by the present invention having the following features.

According to a first aspect of the present invention, there is provided an amino-acid biosensor for measuring a total concentration of a plurality of specific amino acids. The amino-acid biosensor comprises a measuring electrode which include as components, a mediator and an enzyme, which selectively act on at least the plurality of specific amino acids each serving as a substrate, and a counter electrode. In the amino-acid biosensor, the enzyme has a substrate affinity to each of the plurality of specific amino acids. The enzyme is operable to catalyze a reaction in each of the plurality of specific amino acids as a substrate so as to form a reaction product. The mediator is operable, during amino-acid concentration measurement, to carry electrons between the reaction product and the measuring electrode. Further, the amino-acid biosensor is designed to apply a voltage between the measuring electrode and the counter electrode during the measurement in such a manner that, in an analytical curve representing a relationship between an applied voltage and a current value in a specific concentration for each of the plurality of specific amino acids, the applied voltage includes a voltage allowing the variety of the current values for the amino acids in the same concentration and at the same applied voltage to fall within a given range.

According to a second aspect of the present invention, the amino-acid biosensor is further designed to apply a voltage between the measuring electrode and the counter electrode during the measurement in such a manner that, in an analytical curve representing a relationship between an applied voltage and a current value in a specific concentration for each of the plurality of specific amino acids, the applied voltage includes a voltage allowing the variety of the current values for the amino acids in the same concentration and at the same applied voltage to fall within 20% of a maximum current value.

According to a third aspect of the present invention, in the amino-acid biosensor, the measuring electrode further includes a coenzyme as a component, and the enzyme consists of a dehydrogenase. Further, the reaction product consists of a reduced coenzyme derived by reduction of the coenzyme, and the mediator is operable, during the amino-acid concentration measurement, to carry electrons from the reduced coenzyme to the measuring electrode.

According to a forth aspect of the present invention, in the branched-chain-amino-acid biosensor, the plurality of specific amino acids consist of branched-chain amino acids including leucine, valine and isoleucine. Further, the dehydrogenase consists of leucine dehydrogenase, and the coenzyme consists of nicotinamide adenine dinucleotide.

According to a fifth aspect of the present invention, the mediator consists of 1-methoxy-5-methyl-phenazinium methyl sulfate (PMS).

According to a sixth aspect of the present invention, the plurality of specific amino acids consist of aromatic amino acids including phenylalanine and tyrosine, and the dehydrogenase consists of phenylalanine dehydrogenase.

According to a seventh aspect of the present invention, there is provided a Fischer-ratio biosensor comprising the branched-chain-amino-acid biosensor set forth in the fourth aspect of the present invention, the aromatic-amino-acid biosensor set forth in the sixth aspect of the present invention, and Fischer-ratio calculation means for dividing a branched-chain-amino-acid concentration measured using the branched-chain-amino-acid biosensor by an aromatic-amino-acid concentration measured using the aromatic-amino-acid biosensor, to calculate a Fischer ratio.

According to an eighth aspect of the present invention, there is provided a biological information management system comprising biological information management means for managing biological information of a membership, and a membership terminal for allowing the membership to communicate with the biological information management means. In the biological information management system, the biological information management means includes biological-information data management means for managing membership's biological information data including an amino-acid concentration, first receiving means for receiving the amino-acid concentration from the membership terminal via a network, biological information evaluation means for comparing the received amino-acid concentration with a given criterion to derive a biological information evaluation, and first transmission means for transmitting the derived biological information evaluation to the membership terminal via a network. The membership terminal includes the amino-acid biosensor set forth in the first aspect of the present invention, second transmission means for transmitting an amino-acid concentration measured using the amino-acid biosensor, to the biological information management means via a network, second receiving means for receiving the biological information evaluation from the biological information management means via a network, and output means for outputting the received biological information evaluation.

According to a ninth aspect of the present invention, there is provided a health information management system comprising health information management means for managing health information of a membership, and a membership terminal for allowing the membership to communicate with the health information management means. In health information management system, the health information management means includes health-information data management means for managing membership's health information data including a blood branched-chain-amino-acid concentration, first receiving means for receiving the blood branched-chain-amino-acid concentration from the membership terminal via a network, health information evaluation means for comparing the received blood branched-chain-amino-acid concentration with a given criterion to derive a health information evaluation, and first transmission means for transmitting the derived health information evaluation to the membership terminal via a network. The membership terminal includes the branched-chain-amino-acid biosensor set forth in the fourth aspect of the present invention, second transmission means for transmitting a blood branched-chain-amino-acid concentration measured using the branched-chain-amino-acid biosensor, to the health information management means via a network, second receiving means for receiving the health information evaluation from the health information management means via a network, and output means for outputting the received health information evaluation.

According to a tenth aspect of the present invention, there is provided a health information management system comprising health information management means for managing health information of a membership, and a membership terminal for allowing the membership to communicate with the health information management means. In the health information management system, the health information management means includes health-information data management means for managing membership's health information data including a Fischer ratio, first receiving means for receiving the Fischer ratio from the membership terminal via a network, health information evaluation means for comparing the received Fischer ratio with a given criterion to derive a health information evaluation, and first transmission means for transmitting the derived health information evaluation to the membership terminal via a network. The membership terminal includes the Fischer-ratio biosensor set forth in the seventh aspect of the present invention, second transmission means for transmitting a blood amino-acid Fischer ratio measured using the Fischer-ratio biosensor, to the health information management means via a network, second receiving means for receiving the health information evaluation from the health information management means via a network, and output means for outputting the received health information evaluation.

According to an eleventh aspect of the present invention, there is provided a method of measuring a total concentration of a plurality of specific amino acids in a sample solution by use of an amino-acid biosensor comprising a measuring electrode which includes as components a mediator and an enzyme which selectively act on at least the plurality of specific amino acids each serving as a substrate, and a counter electrode, wherein the enzyme has a substrate affinity to each of the plurality of specific amino acids, the enzyme being operable to catalyze a reaction in each of the plurality of specific amino acids as a substrate so as to form a reaction product, and the mediator being operable, during amino-acid concentration measurement, to carry electrons between the reaction product and the measuring electrode. The method comprises the steps of allowing the amino-acid biosensor to come into contact with the sample solution; applying, between the measuring electrode and the counter electrode, a voltage configured such that, in an analytical curve representing a relationship between an applied voltage and a current value in a specific concentration for each of the plurality of specific amino acids, the variety of the current values for the amino acids in the same concentration and at the same applied voltage falls within a given range; measuring a response current value generated between the measuring electrode and the counter electrode under the applied voltage; and determining an amino-acid concentration corresponding to the applied voltage and the response current value in the analytical curve, as a total concentration of the plurality of specific amino acids in the sample solution.

According to a twelfth aspect of the present invention, there is provided a health-index measurement method for deriving a health index from a human-originated sample solution by use of: a first amino-acid biosensor comprising a measuring electrode which includes as components a mediator and an enzyme which selectively act on at least a plurality of specific amino acids each serving as a substrate, and a counter electrode, wherein the enzyme has a substrate affinity to each of the plurality of specific amino acids, the enzyme being operable to catalyze a reaction in each of the plurality of specific amino acids as a substrate so as to form a reaction product, and the mediator being operable, during amino-acid concentration measurement, to carry electrons between the reaction product and the measuring electrode; and a second amino-acid biosensor comprising a measuring electrode which includes as components a mediator and an enzyme which selectively act on a substrate consisting of a single amino acid other than the plurality of specific amino acids, and a counter electrode, wherein the enzyme is operable to catalyze a reaction in the single amino acid as a substrate so as to form a reaction product, and the mediator is operable, during the amino-acid concentration measurement, to carry electrons between the reaction product and the measuring electrode. The health-index measurement method comprises the steps of: allowing the first and second amino-acid biosensors to come into contact with the human-originated sample solution; applying, between the measuring and counter electrodes of the first amino-acid biosensor, a voltage configured such that, in an analytical curve representing a relationship between an applied voltage and a current value in a specific concentration for each of the plurality of specific amino acids, the variety of the current values for the plurality of specific amino acids in the same concentration and at the same applied voltage falls within a given range; measuring a response current value generated between the measuring and counter electrodes of the first amino-acid biosensor under the applied voltage; determining an amino-acid concentration corresponding to the applied voltage and the response current value in the analytical curve, as a total concentration of the plurality of specific amino acids in the sample solution; applying a given voltage between the measuring and counter electrodes of the second amino-acid biosensor; measuring a response current value generated between the measuring and counter electrodes of the second amino-acid biosensor under the applied voltage; determining an amino-acid concentration corresponding to the given applied voltage and the response current value, as a concentration of the single amino acid in the sample solution; and deriving a given health index by a given calculation using input information consisting of the determined total concentration of the plurality of specific amino acids and the determined concentration of the single amino acid.

According to a thirteenth aspect of the present invention, there is provided a health-index measurement method for deriving a health index from a human-originated sample solution by use of: a first amino-acid biosensor comprising a measuring electrode which includes as components a mediator and an enzyme which selectively act on at least a first plurality of specific amino acids each serving as a substrate, and a counter electrode, wherein the enzyme has a substrate affinity to each of the first plurality of specific amino acids, the enzyme being operable to catalyze a reaction in each of the first plurality of specific amino acids as a substrate so as to form a reaction product, and the mediator being operable, during amino-acid concentration measurement, to carry electrons between the reaction product and the measuring electrode; and a second amino-acid biosensor comprising a measuring electrode which includes as components a mediator and an enzyme which selectively act on a substrate consisting of a second plurality of specific amino acids other than the first plurality of specific amino acids, and a counter electrode, wherein the enzyme has a substrate affinity to each of the second plurality of specific amino acids, the enzyme being operable to catalyze a reaction in each of the second plurality of specific amino acids as a substrate so as to form a reaction product, and the mediator being operable, during the amino-acid concentration measurement, to carry electrons between the reaction product and the measuring electrode. The health-index measurement method comprises the steps of: allowing the first and second amino-acid biosensors to come into contact with the human-originated sample solution; applying, between the measuring and counter electrodes of the first amino-acid biosensor, a voltage configured such that, in a first analytical curve representing a relationship between an applied voltage and a current value in a specific concentration for each of the first plurality of specific amino acids, the variety of the current values for the first plurality of specific amino acids in the same concentration and at the same applied voltage falls within a given range; measuring a response current value generated between the measuring and counter electrodes of the first amino-acid biosensor under the applied voltage; determining an amino-acid concentration corresponding to the applied voltage and the response current value in the first analytical curve, as a total concentration of the first plurality of specific amino acids in the sample solution; applying, between the measuring and counter electrodes of the second amino-acid biosensor, a voltage configured such that, in a second analytical curve representing a relationship between an applied voltage and a current value in a specific concentration for each of the second plurality of specific amino acids, the variety of the current values for the second plurality of specific amino acids in the same concentration and at the same applied voltage falls within a given range; measuring a response current value generated between the measuring and counter electrodes of the second amino-acid biosensor under the applied voltage; determining an amino-acid concentration corresponding to the applied voltage and the response current value in the second analytical curve, as a total concentration of the second plurality of specific amino acids in the sample solution; and deriving a given health index by a given calculation using input information consisting of the determined total concentration of the first plurality of specific amino acids and the determined total concentration of the second plurality of specific amino acids.

According to a fourteenth aspect of the present invention, there is provided a health-index measurement method for deriving a health index from a human-originated sample solution by use of: an amino-acid biosensor comprising a measuring electrode which includes as components a mediator and an enzyme which selectively act on at least a plurality of specific amino acids each serving as a substrate, and a counter electrode, wherein the enzyme has a substrate affinity to each of the plurality of specific amino acids, the enzyme being operable to catalyze a reaction in each of the plurality of specific amino acids as a substrate so as to form a reaction product, and the mediator being operable, during amino-acid concentration measurement, to carry electrons between the reaction product and the measuring electrode; and a biological-component biosensor comprising a measuring electrode which includes as components a mediator and an enzyme adapted to selectively act on a substrate consisting of a specific biological component, and a counter electrode, wherein the enzyme is operable to catalyze a reaction in the biological component as a substrate so as to form a reaction product, and the mediator is operable, during the biological-component concentration measurement, to carry electrons between the reaction product and the measuring electrode. The health-index measurement method comprises the steps of: allowing the amino-acid and biological-component biosensors to come into contact with the human-originated sample solution; applying, between the measuring and counter electrodes of the amino-acid biosensor, a voltage configured such that, in an analytical curve representing a relationship between an applied voltage and a current value in a specific concentration for each of the plurality of specific amino acids, the variety of the current values for the amino acids in the same concentration and at the same applied voltage falls within a given range; measuring a response current value generated between the measuring and counter electrodes of the amino-acid biosensor under the applied voltage; determining an amino-acid concentration corresponding to the applied voltage and the response current value in the analytical curve, as a total concentration of the plurality of specific amino acids in the sample solution; applying a given voltage between the measuring and counter electrodes of the biological-component biosensor; measuring a response current value generated between the measuring and counter electrodes of the biological-component biosensor under the applied voltage; determining a biological-component concentration corresponding to the given applied voltage and the response current value, as a concentration of the biological component in the sample solution; and deriving a given health index by a given calculation using input information consisting of the determined total concentration of the plurality of specific amino acids and the determined concentration of the biological component.

According to a fifteenth aspect of the present invention, the biological component includes two or more types, and two or more of the biological-component sensors are provided correspondingly to the respective two or more types of biological components.

According to the present invention, the amino-acid biosensor (200) for measuring a total concentration of a plurality of specific amino acids comprises the measuring electrode (202) which include as components a mediator and an enzyme which selectively act on at least the plurality of specific amino acids each serving as a substrate, and the counter electrode (203). The enzyme has a substrate affinity to each of the plurality of specific amino acids. The enzyme is operable to catalyze a reaction in each of the plurality of specific amino acids as a substrate so as to form a reaction product. The mediator is operable, during amino-acid concentration measurement, to carry electrons between the reaction product and the measuring electrode. Further, the amino-acid biosensor is designed to apply a voltage between the measuring electrode and the counter electrode during the measurement in such a manner that, in an analytical curve representing a relationship between an applied voltage and a current value in a specific concentration for each of the plurality of specific amino acids, the applied voltage includes a voltage allowing the variety of the current values for the amino acids at the same applied voltage to fall within a given range. This makes it possible to provide an amino-acid biosensor capable of measuring a total concentration of plural types of amino acids using a single electrode system.

According to the present invention, in the above amino-acid biosensor, leucine dehydrogenase is used as the enzyme, and nicotinamide adenine dinucleotide is used as the coenzyme. This makes it possible to measure a concentration of branched-chain amino acids using a single electrode system. Further, PMS may be used as the mediator to perform the measurement with a higher degree of accuracy.

According to the present invention, the branched-chain-amino-acid biosensor and the aromatic-amino-acid biosensor each capable of performing the measurement in the form of a single electrode system are combined together, and a measured branched-chain-amino-acid concentration is divided by a measured aromatic-amino-acid concentration to calculate a Fischer ratio. This makes it possible to provide a Fischer-ratio biosensor capable of measuring a Fischer ratio by a single measurement operation.

According to the present invention, a user transmits a Fischer ratio measured using the Fischer-ratio biosensor on an individual basis, from a user terminal (502) to a server (506), and the server compares the Fischer ratio with a reference value to make an evaluation and a comment and displays the evaluation and comment on the user terminal. This makes it possible to establish a health management system utilizing a Fischer ratio which could be sufficiently utilized due to difficulty in measurement thereof.

Further, the present invention makes it possible to provide a method of measuring a total concentration of plural types of amino acids using an amino-acid sensor having a single electrode system, a method of measuring a health index, such as a BTR value to be calculated from a concentration of a single amino acid and a total concentration of plural types of amino acids, or a Fischer ratio to be calculated from a total concentration of a first plurality of specific amino acids and a total concentration of a second plurality of specific amino acids, using an amino-acid biosensor, and a method of measuring a health index to be calculated from a total concentration of plural types of amino acids and a concentration of one or more types of biological components.

BRIEF DESCRIPTION OF THE DRAWINGS

FIG. 13 is a schematic diagram showing a membership registration screen.

FIG. 14 is a schematic diagram showing a measured-value output screen.

Figure 1:
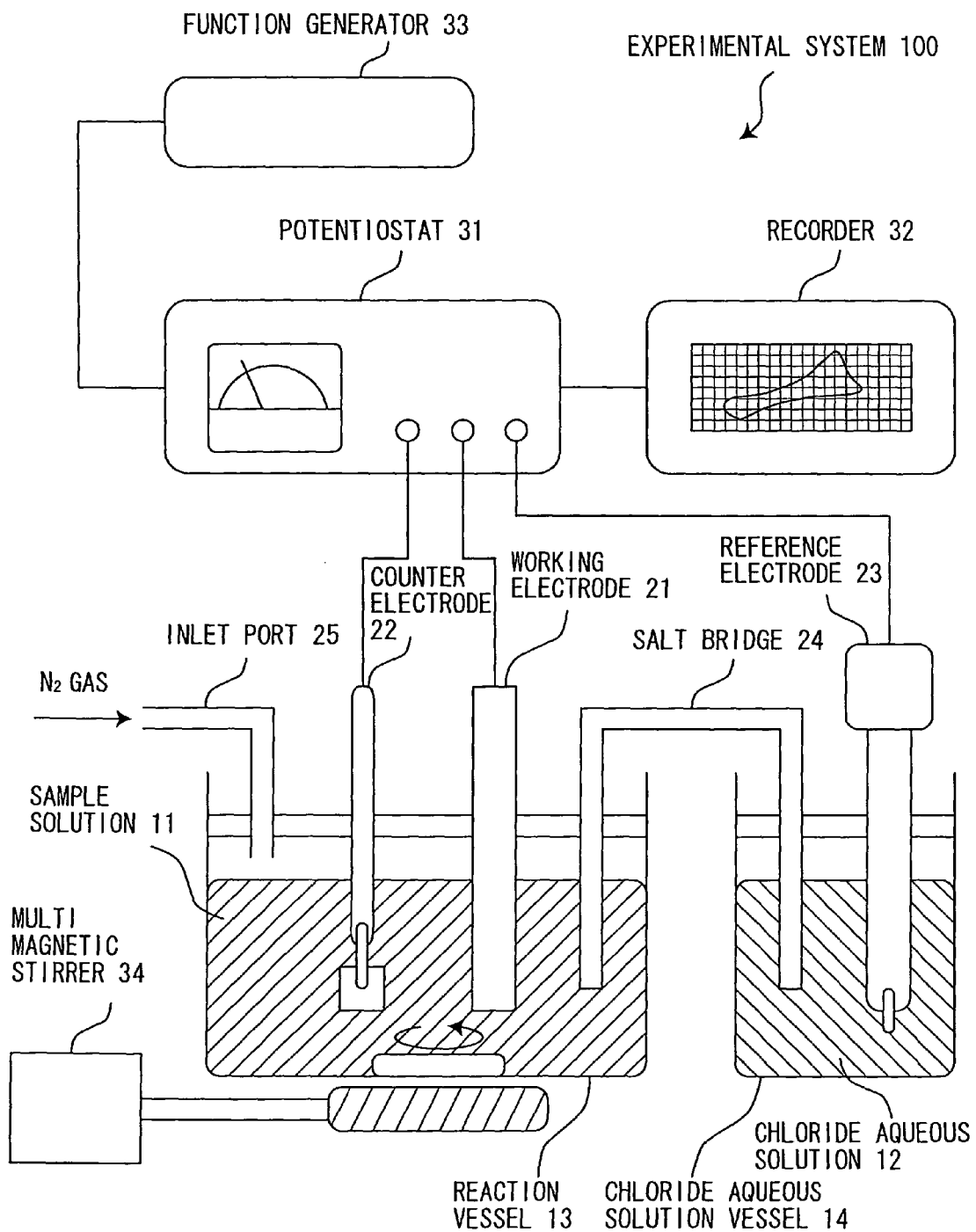
FIG. 1 is a schematic block diagram showing an experimental system 100.

BEST MODE FOR CARRYING OUT THE INVENTION (Configuration of Experimental System)

As used in the specification, the term "health index" means a total concentration of plural types of amino acids measured by a biosensor of the present invention, or an index calculated using the total concentration. The index calculated from a total concentration of plural types of amino acids may be an index calculated from a total concentration of a first plurality of specific amino acids and a total concentration of a second plurality of specific amino acids, or from a total concentration of plural types of amino acids and a concentration of a single different amino acid. For example, a health index calculated from respective total concentrations of two different types of amino acids includes a Fischer ratio, and a health index calculated from a total concentration of plural types of amino acids and a concentration of a single different amino acid includes a BTR value.

As used in the specification, the term "a plurality of specific amino acids" to be measured by the biosensor of the present invention may include plural types of amino acids each serving as a common substrate for a single enzyme. For example, a plurality of specific amino acids each serving as a substrate for leucine dehydrogenase include branched-chain amino acids (BCAAs) consisting of valine, leucine and isoleucine, and a plurality of specific amino acids each serving as a common substrate for phenylalanine dehydrogenase include aromatic amino acids consisting of tyrosine and phenylalanine.

A typical oxidation/reduction reaction formula of an α-amino acid using nicotinamide adenine dinucleotide (NAD) as a coenzyme is expressed as follows:

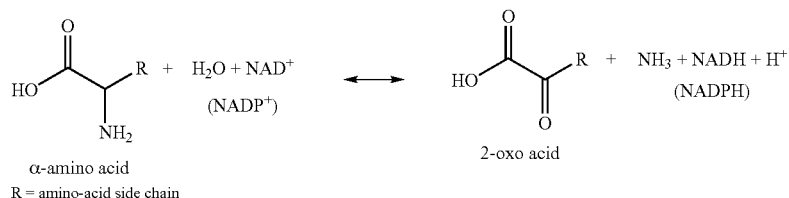

α-amino acid
R = amino-acid side chain 2-oxo acid

An oxidation/reduction reaction formula of L-phenylalanine using phenylalanine dehydrogenase as an enzyme and NAD as a coenzyme is expressed as follows:

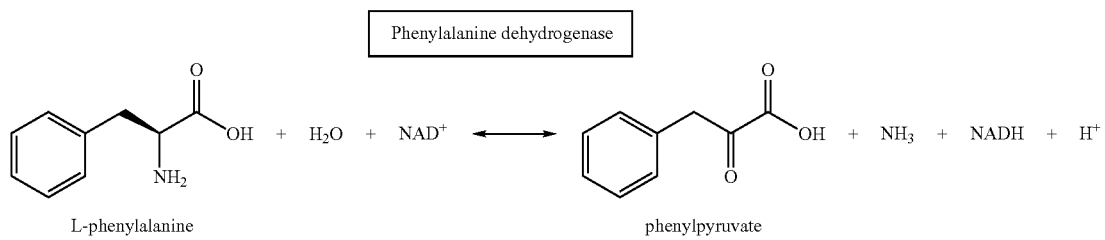

L-phenylalanine phenylpyruvate

An oxidation/reduction reaction formula of L-leucine using leucine dehydrogenase as an enzyme and NAD as a coenzyme is expressed as follows:

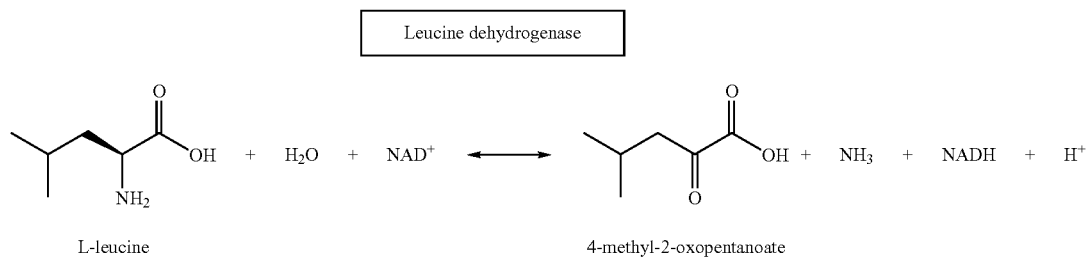

L-leucine 4-methyl-2-oxopentanoate

In the following description, a Fischer ratio and a BTR value will be referred to collectively as "Fischer ratio". Any enzyme having reactivity with a plurality of specific amino acids and allowing electron exchange during the reaction is usable in the present invention, and appropriately selected depending on intended measuring objects. The enzyme usable in the present invention may be a commercially available enzyme or may be an enzyme extracted from a microorganism. A variant enzyme appropriately altered or modified by a genetic engineering technique or the like may be used to provide enhanced substrate specificity and/or reactor rate. For example, an enzyme which is known as one generally having reactivity with a single substrate may be modified to have reactivity with plural types of substrates. For example, the enzyme having reactivity with a plurality of specific amino acids and allowing electron exchange during the reaction includes an enzyme capable of catalyzing a reaction involving an oxidation/reduction reaction, such as dehydrogenase or oxidoreductase, specifically, leucine dehydrogenase, tyrosine dehydrogenase, phenylalanine dehydrogenase, leucine oxidoreductase, tyrosine monooxygenase, alanine dehydrogenase and glutamate dehydrogenase. An enzyme having reactivity with a biological component other than an amino acid and allowing electron exchange during the reaction includes an enzyme capable of catalyzing a reaction involving an oxidation/reduction reaction, such as dehydrogenase or oxidoreductase, specifically, alcohol dehydrogenase, cholesterol dehydrogenase, isocitric dehydrogenase and glucose dehydrogenase.

While the enzyme to be used in the present invention is adapted to catalyze a reaction involving electron exchange, such a reaction can involve a reaction catalyzed by a coenzyme. A preferred coenzyme includes reduced nicotinamide adenine dinucleotide (NADH) and reduced nicotinamide adenine dinucleotide phosphate (NADPH).

In the present invention, based on an experimental system 100 using a reaction vessel, it was verified that a total concentration of branched-chain amino acids can be measured using a biosensor having a single electrode system. FIG. 1 is a schematic block diagram showing the experimental system 100 used for the experimental test. The experimental system 100 is formed as a 3-electrode type electrochemical cell. The experimental system 100 comprises a sample solution 11, a chloride aqueous solution 12, a reaction vessel 13, a chloride aqueous solution vessel 14, a working electrode 21, a counter electrode 22, a reference electrode 23, a salt bridge 24, an inlet port 25, a potentiostat 31, a recorder 32, a function generator 33 and a multi magnetic stirrer 34. The sample solution 11 is prepared by dissolving an amino acid to be measured, an enzyme having a substrate affinity to the amino acid, a coenzyme adapted to cooperate with the enzyme and a mediator in appropriate concentrations. The chloride aqueous solution 12 forms a cell in cooperation with the reference electrode 23 to allow a reference voltage to be generated from the reference electrode 23. The working electrode 21 is operable to cause a chemical reaction in response to a given voltage applied between the working electrode 21 and the counter electrode 22. A possibility of quantification of the amino acid can be determined by measuring a current flowing during the reaction. The salt bridge 24 is provided as a means to keep the reaction vessel 13 and the chloride aqueous solution vessel 14 at the same potential so as to allow a potential of the reference electrode 23 to be used for correction of the working electrode 21. The inlet port 25 is used for introducing nitrogen gas to an upper space of reaction vessel 13 therethrough to maintain a smooth reaction in the reaction vessel 13. The potentiostat 31 is designed to measure a voltage-current characteristic under the condition that a current flows while keeping a voltage at a given value. Specifically, the potentiostat 31 is operable to measure a current while changing a voltage according to a time-voltage curve programmed in the function generator 33. The recorder 32 is operable to record a measurement result of the potentiostat 31. The multi magnetic stirrer 34 is operable to stir the sample solution 11 in the reaction vessel 13.

(Experimental System)

In the experiments, a voltage-current characteristic of the sample solution 11 between the working electrode 21 and the counter electrode 22 in the experimental system 100 was measured while changing respective concentrations of the amino acid and other component in the sample solution 11. A branched-chain amino acid, specifically, one of leucine, isoleucine and valine, or a mixture thereof, was used as the amino acid. Typically, an electrochemical measurement of an amino-acid concentration is performed by causing a reaction in a target amino acid using an enzyme, and measuring a concentration of a reaction product formed through the reaction. The reaction product subject to the concentration measurement may be a substance changed from the amino acid itself through the reaction or may be a by-product formed during the reaction of the amino acid. Generally, a concentration of a by-product is measured in many cases. The concentration measurement is typically performed by measuring a current flowing when a certain voltage is applied to the sample solution, and determining a concentration based on the obtained voltage-current characteristic. Further, in the by-product concentration measurement, it is often the case that a mediator adapted to carry electrons between the by-product and the electrode is used, and a current flowing through the medium of the mediator is measured. In this example, leucine dehydrogenase, a dehydrogenase of leucine, was used as the enzyme. The leucine dehydrogenase derived from *Bacillus stearothermophilus*, a moderate thermophilic bacteria, is an enzyme operable to oxidize leucine through a dehydrogenation reaction. The leucine dehydrogenase has a substrate affinity to not only leucine but also isoleucine and valine. Thus, the leucine dehydrogenase also causes or catalyzes a dehydrogenation reaction in isoleucine and valine. In the dehydrogenation reaction of leucine (and isoleucine/valine), nicotinamide adenine dinucleotide (hereinafter referred to shortly as "NAD") acts as a coenzyme, and NAD itself is reduced and changed to reduced nicotinamide adenine dinucleotide (hereinafter referred to shortly as "NADH"). A concentration of NADH can be measured to determine a concentration of an amino acid, such as leucine.

When an enzyme which catalyze a dehydrogenation reaction of an amino acid other than branched-chain amino acids, nicotinamide adenine dinucleotide phosphate (hereinafter referred to shortly as "NADP") acts as a coenzyme in some cases. In this case, a concentration of reduced nicotinamide adenine dinucleotide phosphate (hereinafter referred to shortly as "NADPH") resulting from reduction of NADP can be measured to determine a concentration of the target amino acid. The formed NADH has a property of releasing H to cause susceptibility to oxidation. Thus, an oxidation reaction is caused at a positive-side working electrode to allow electrons to flow in the working electrode, and the resulting current can be measured to determine an amount of formed NADH, i.e., an amount of oxidized leucine. In this connection, it is known that an oxidation reaction rate of NADH on an electrode is low. Thus, a mediator adapted to carry electrons is typically interposed between NADH and the electrode so as to allow electrons to be given from NADH to the electrode through the mediator. In this process, NADH gives electrons to the electrode, or is oxidized, and returns to NAD. In this experimental test, a current was measured in a state after adding a mediator to the sample solution 11. While a stand-alone biosensor is typically designed to fix an enzyme, a coenzyme and a mediator to a working electrode thereof, each of the enzyme, coenzyme and mediator were dissolved in the sample solution 11 in this experimental test.

(Selection of Suitable Mediator)

A test for selecting a suitable mediator was firstly performed in an alkaline state (pH 10.5) which is an optimal reaction condition for the above leucine dehydrogenase. (1) Meldola's Blue (hereinafter referred to shortly as "MB"), (2) 1-methoxy-5-methylphenazinium methyl sulfate (hereinafter referred to shortly as "PMS") and (3) pyrroloquinoline quinone (hereinafter referred to shortly as "PQQ") were used as a candidate for a suitable mediator. An optimal reaction condition is varied depending on a selected enzyme, and therefore a mediator has to be appropriately selected in conjunction with the selection of an enzyme. Except for this requirement, the mediator is not limited to a specific type, but any substance capable of being electrochemically reduced by NADH or NADPH formed through an enzymatic reaction and oxidized by the electrode may be used as the mediator. For example, the mediator may be appropriately selected from the group consisting of quinones, cytochromes, ferredoxins and ferrocenes and derivatives thereof For each of the mediators, two voltage-current characteristics were measured in respective cases of using only a mediator and of adding NADH to the mediator, by a conventional method for figuring out an electrochemical characteristic under the above conditions, and compared with each other. According to a conventional method, the voltage-current characteristics were measured using the potentiostat while gradually changing a voltage. NADH is formed through an enzymatic reaction, depending on a concentration of a target amino acid to be measured, and therefore the concentration of the target amino acid can be determined by measuring NADH. The following description will be made about one example of a preliminary assay for selecting a mediator. Thus, the present invention is not limited to this example, but a mediator to be actually selected can be changed depending on other condition, such as a measurement target or a selected enzyme. In the selection of a mediator, two voltage-current characteristics are measured in respective cases of using only a mediator and of adding NADH to the mediator, and expressed in graph form to readily figure out features thereof. It may be considered that these graphs indicate to what degree the mediator reacts with NADH. That is, a large difference in shape between two graph curves in the respective case of using only the mediator and of adding NADH to the mediator means that the voltage-current characteristic is changed sensitively in response to the presence of NADH, and the mediator is suitable for measuring an NADH concentration and an amino-acid concentration. As to the difference between the graph curves, if the graph curves are different from each other in an overall shape in addition to the absolute value, the mediator may be considered to be more suitable for measuring an NADH concentration, by the following reason. In the measurement using the potentiostat, when an applied voltage to the electrode is shifted in a positive direction from an equilibrium potential of the sample solution, a reaction on the electrode is moved toward an oxidation reaction, and thereby an anode current flows through the electrode. Conversely, when an applied voltage to the electrode is shifted in a negative direction from the equilibrium potential the sample solution, a reaction on the electrode is moved toward a reduction reaction, and thereby a cathode current flows through the electrode. Thus, both a reaction and a location (electrode) of the reaction during increase of the applied voltage will become different from those during reduction of the applied voltage. If a mediator acts specifically on a reaction product (NADH in this example), a voltage-current characteristic curve must be largely changed in shape depending on whether NADH is present or absent. The reason is that, when an applied voltage reaches a value which allows the mediator to initiate an oxidation/reduction reaction specifically with the reaction product, a current value will be sharply increased if NADH is added, but such a sharp change never occurs if no NADH is added. Thus, a large difference in shape between the graph curves means that the mediator causes an NADH-specific reaction, and a change in the voltage-current characteristic adequately reflect a change in NADH concentration.

Based on MB, PMS and PQQ, various conditions were appropriately set, and the above voltage-current characteristics were measured and compared with each other. Under the set conditions, it was verified that graph curves for MB or PMS are largely changed in absolute value and shape, depending on whether NADH is present or absent. Thus, in view of the graph of the analytical curves obtained under the set condition, MB or PMS was tentatively considered to be suitable as a mediator.

However, MB without modification is considered to be unsuitable for a mediator, by the following reason. As mentioned above, an optimal reaction condition for leucine dehydrogenase is an alkaline state of about pH 10.5. While pH was adjusted at such a value to perform a test, it was proven that, in the alkaline state, MB will be insolubilized over time and finally precipitated. Thus, MB without modification is considered to be unsuitable for a mediator for leucine dehydrogenase. As a measure of allowing MB to be usable as a mediator, it is contemplated to use MB in the presence of a compound capable of preventing insolubilization of MB. The following measurements were performed using PMS as a mediator.

(PMS Concentration—Specificity for NADH)

In order to clarify a suitable concentration range of PMS to be used as a mediator, voltage-current characteristics were measured in respective cases where NADH is added and not added, using a PMS concentration as a parameter. Based on the measurement result, a level of difference between respective voltage-current characteristics in the two cases of NADH is present and absent, i.e., a PMS-concentration dependence of specificity for NADH, can be known. That is, a PMS concentration causing a large change in current value depending on the presence or absence of NADH can be determined.

Figure 2:
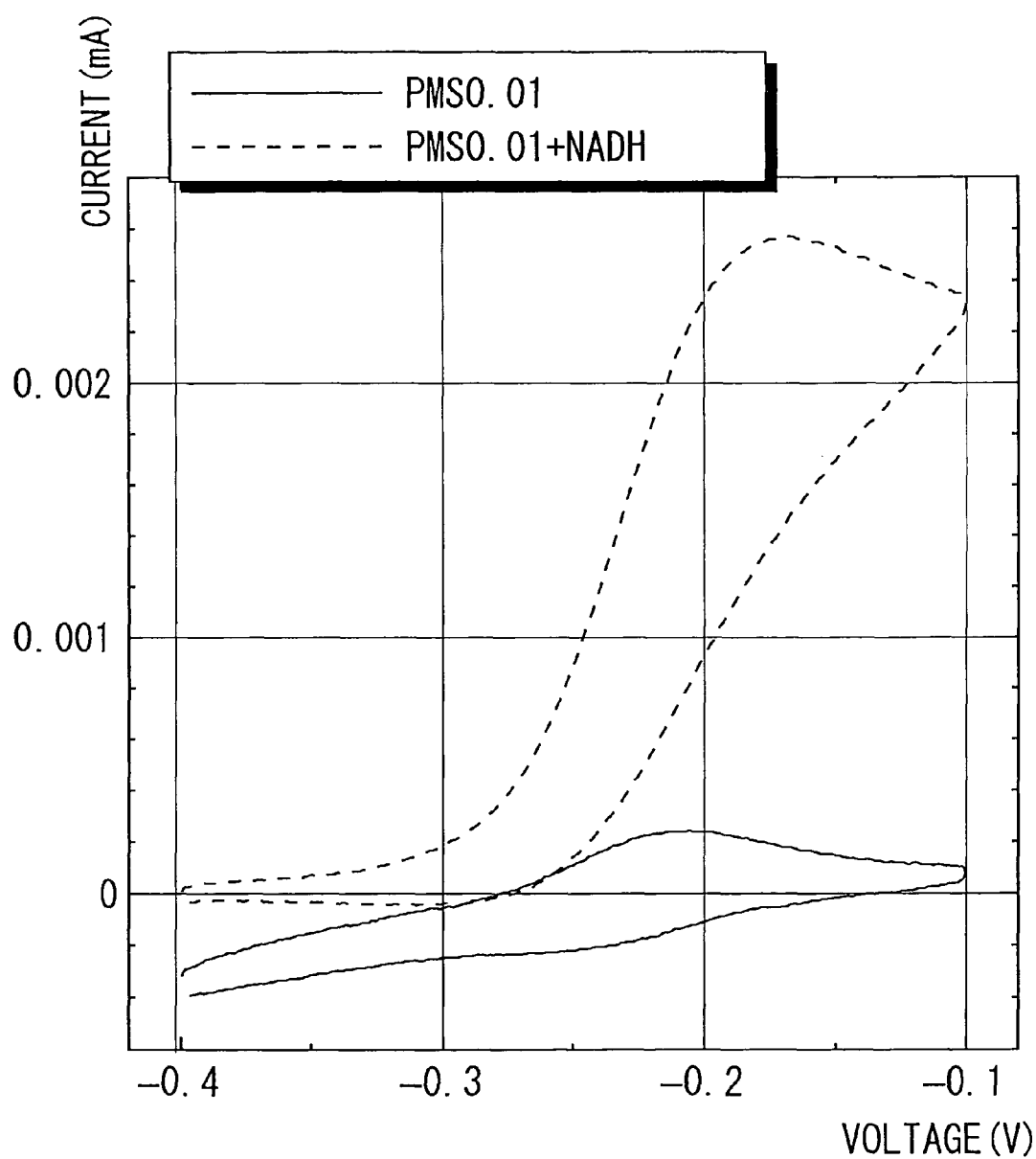
FIG. 2 is a graph showing voltage-current characteristics in respective cases where NADH is present and absent under the condition that a PMS concentration is kept at 0.01 mM.
Figure 3:
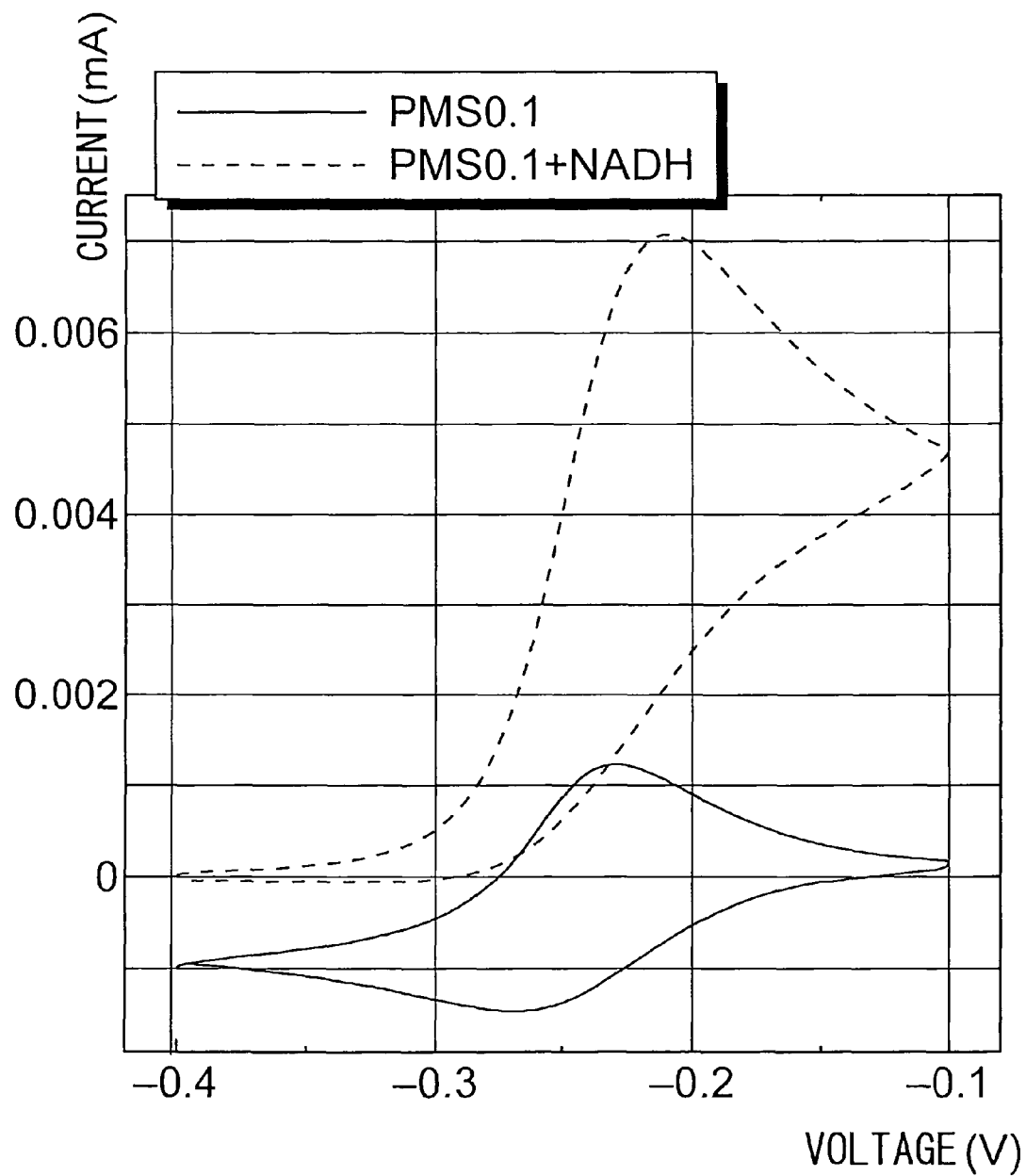
FIG. 3 is a graph showing voltage-current characteristics in respective cases where NADH is present and absent under the condition that a PMS concentration is kept at 0.1 mM.
Figure 4:
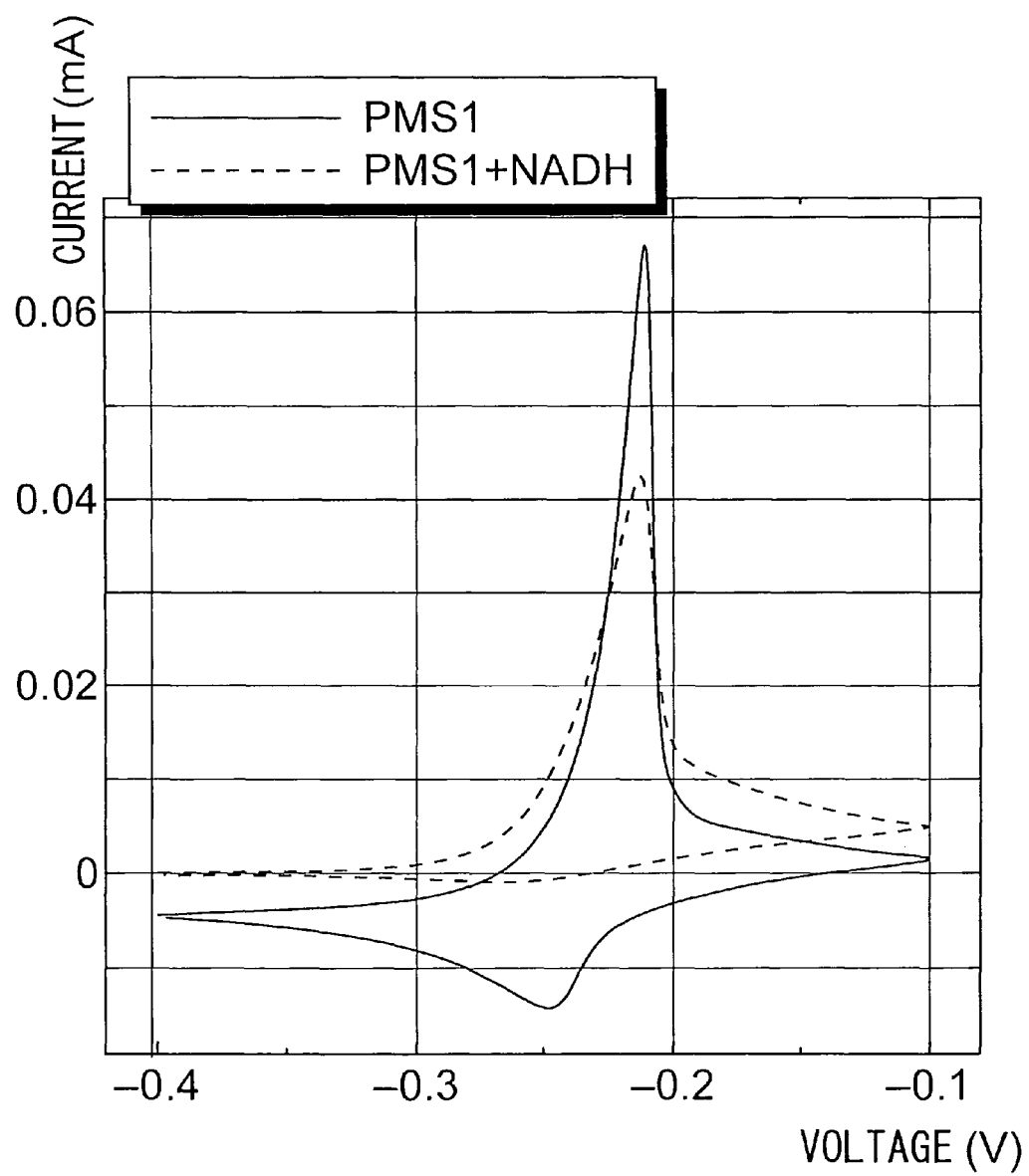
FIG. 4 is a graph showing voltage-current characteristics in respective cases where NADH is present and absent under the condition that a PMS concentration is kept at 1 mM.
Figure 5:
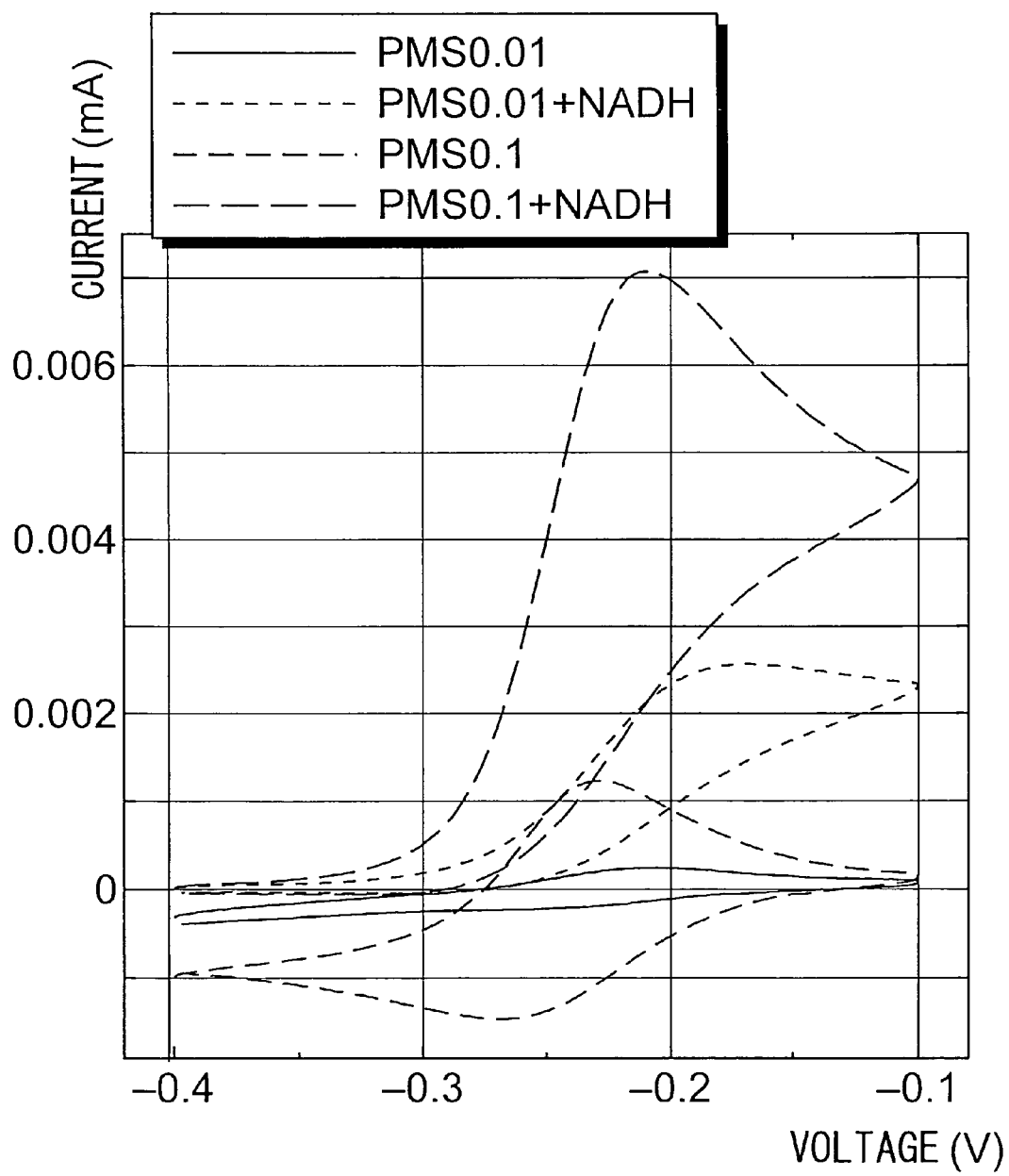
FIG. 5 is a graph showing voltage-current characteristics in respective cases where NADH is present and absent under the conditions that a PMS concentration is kept at 0.01 mM and 0.1 mM.

FIG. 2 is a graph showing voltage-current characteristics in respective cases where NADH is present and absent under the condition that a PMS concentration is kept at 0.01 mM. FIGS. 3 and 4 are graphs in the same conditions except that a PMS concentration is kept at 0.1 mM and 1 mM, respectively. FIG. 5 is a graph collectively showing the characteristics under the conditions that a PMS concentration is kept at 0.01 mM and 0.1 mM. These graphs show one example of a preliminary assay for setting a mediator concentration. Thus, the present invention is not limited to this example, but an actual mediator concentration can be changed depending on other conditions. As seen in FIG. 2, when the PMS concentration is 0.01 mM, while a current in the case of the absence of NADH is in the range of −0.0004 mA to 0.0003 mA, a current in the case of the presence of NADH is in the range of 0 mA to 0.0025 mA, i.e., the range is increased to about 3.5 times. Further, a current peak value is increased from 0.0003 mA to 0.0025 mA, i.e., increased to about 8 times. As seen in FIG. 3, when the PMS concentration is 0.1 mM, while a current in the case of the absence of NADH is in the range of −0.0015 mA to 0.0012 mA, a current in the case of the presence of NADH is in the range of 0 mA to 0.007 mA, i.e., the range is increased to about 2.5 times. Further, a current peak value is increased from 0.0012 mA to 0.007 mA, i.e., increased to about 6 times. Further, as seen in FIG. 4, when the PMS concentration is 1 mM, while a current in the case of the absence of NADH is in the range of −0.015 mA to 0.07 mA, a current in the case of the presence of NADH is in the range of 0 mA to 0.04 mA, i.e., the range is reduced to about one-half. Further, a current peak value is reduced from 0.07 mA to 0.04 mA, i.e., reduced to about one-half. As above, when the PMS concentration is 0.01 mM and 0.1 mM, each of the current range and the current peak value is increased to several times. Thus, it can be said that PMS in these concentrations has high specificity for NADH, and suitability for measuring an NADH concentrations. In contrast, when the PMS concentration is 1 mM as shown in FIG. 5, each of the current range and the current peak value is not increased but rather reduced. Thus, PMS in this concentration is not suitable for measuring an NADH concentration. Thus, it was verified that PMS exhibits highly suitable characteristics for measuring an NADH concentration when the PMS concentration is kept in the range of about 0.01 to 0.1 mM under the above experimental conditions. What is important is that a relationship between the PMS concentration and the specificity for NADH can be clarified in the above manner to obtain a suitable PMS concentration for measuring an NADH concentration.

(Voltage-Current Characteristic)

Figure 6:
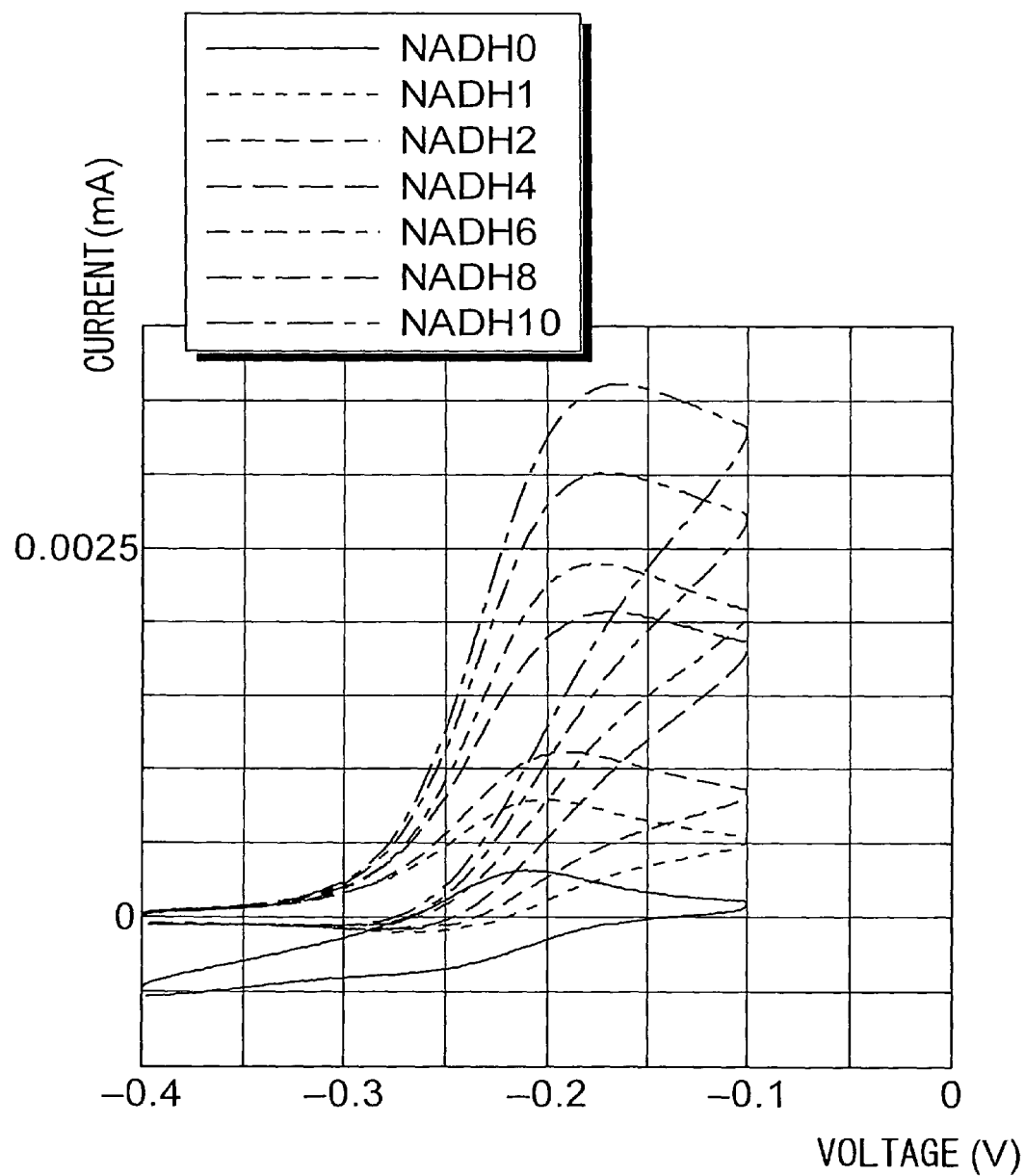
FIG. 6 is a graph showing voltage-current characteristics in a case where a current is measured while changing a voltage under the condition that a NADH concentration is kept at a constant value.

A relationship between a voltage and a current was measured using a NADH concentration as a parameter. A measurement point is set in a voltage range including a condition that a current value is largely changed depending on the NADH concentration (i.e., including a region where the current has a large value relative to the NADH concentration) in this voltage-current characteristic, so that the current at a certain NADH concentration can be increased, i.e., an increment in current relative to the NADH concentration can be increased. That is, the measurement point can be set in a range including the above region where the current has a large absolute value, to obtain enhanced measurement accuracy. FIG. 6 is a graph showing voltage-current characteristics in a case where a current is measured while changing a voltage under the condition that the NADH concentration is kept at a constant value. This graph shows one example of a preliminary assay for setting a voltage-current characteristic. Thus, the present invention is not limited to this example, but a voltage-current characteristic to be actually set can be changed depending on types of a selected mediator and coenzyme and other condition. The NADH concentration was set at 0 mM, 1 mM, 2 mM, 4 mM, 6 mM, 8 mM and mM. As seen in FIG. 6, when the measurement point is set around −0.2 V, a large current value can be measured to obtain enhanced measurement accuracy.

(NADH Concentration-Current Characteristic)

Figure 7:
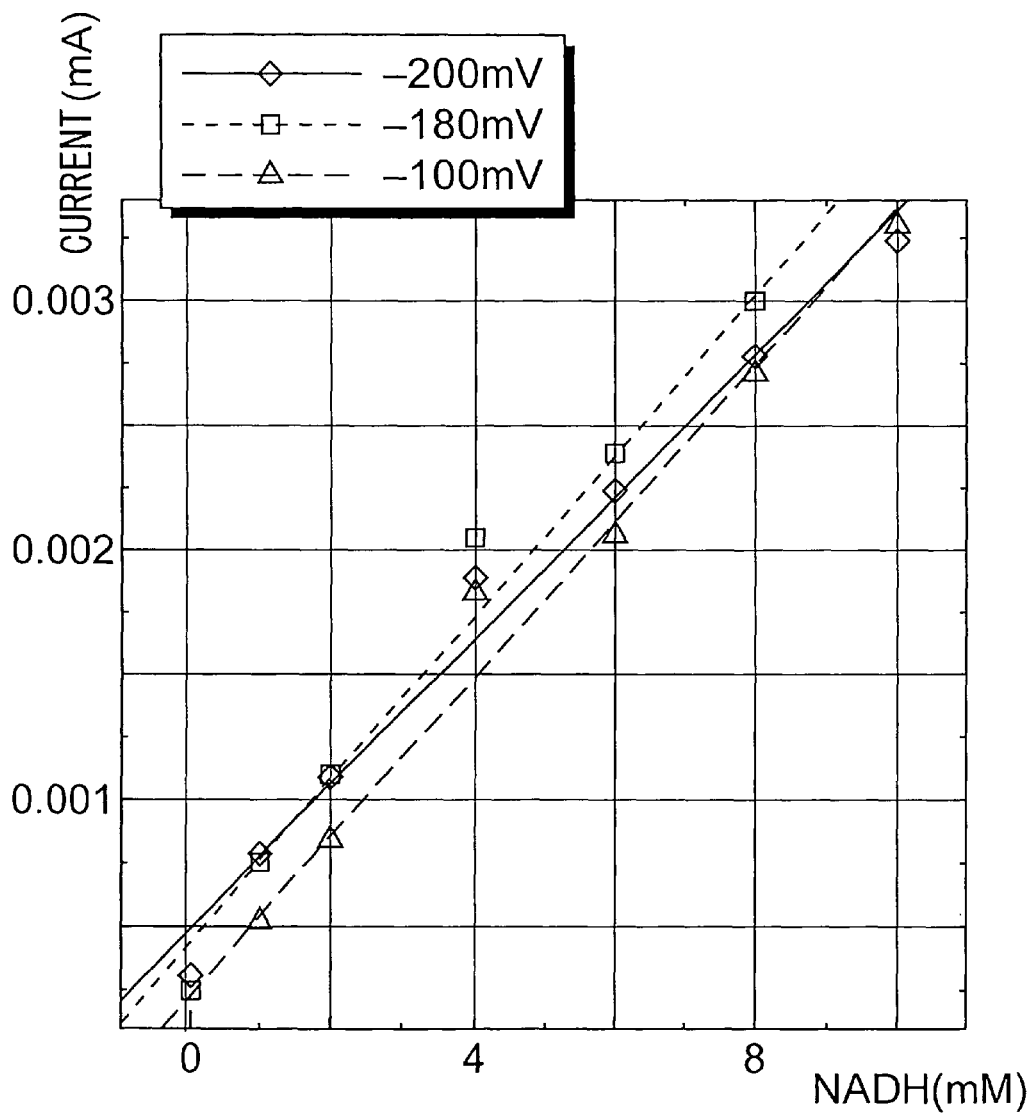
FIG. 7 is a graph showing NADH concentration-current characteristics in a case where a current is measured while changing a NADH concentration under the condition that a voltage is kept at a constant value.

A relationship between a NADH concentration and a current was measured using an applied voltage as a parameter. A condition where the NADH concentration and the current have a linear relationship therebetween is equivalent to a condition where the current is linearly changed in response to a change in the NADH concentration. This condition is desirable in view of the measurement. Thus, it was measured whether there is a voltage value providing such a linear relationship between the NADH concentration and the current. FIG. 7 is a graph showing NADH concentration-current characteristics in a case where a current is measured while changing a NADH concentration under the condition that the voltage is kept at a constant value. The voltage was set at −200 mV, −180 mV and −100 mV. This graph shows one example of a preliminary assay for setting a voltage and a coenzyme concentration. Thus, the present invention is not limited to this example, but a voltage and a coenzyme concentration to be actually set can be changed depending on types and concentrations of a selected mediator and coenzyme and other condition. As seen in FIG. 7, the NADH concentration and the current are approximately in proportionality relation at either of the voltages. This shows that PMS can provide a highly desirable characteristic to the NADH concentration measurement at any voltage.

(Comparison Between Voltage-Current Characteristics of Branched-Chain Amino Acids)

Respective voltage-current characteristics of branched-chain amino acids were measured. A current value at an applied voltage during measurement of an amino acid represents a level of a reaction between the amino acid and an enzyme, i.e., has close connections in a level of substrate affinity and a reaction rata of the enzyme to the amino acid. Each of leucine, isoleucine and valine must exhibit a different value in the level of substrate affinity and the reaction rata to leucine dehydrogenase, and therefore must have a different current at a certain applied voltage. However, if respective voltage-current characteristics of the three types of amino acids, or leucine, isoleucine and valine, are similar to each other to some extent, respective concentrations of the amino acids can be measured by a common experimental system. If so, a total concentration of the three types of amino acids can also be simultaneously measured by a single operation using an amino-acid biosensor having a single electrode system. Further, if there is a certain degree of difference between the voltage-current characteristics, the applied voltage can be set at a value allowing the variety of respective current values of the three types of amino acids at the same applied voltage to fall within a given range. If the given range is permitted as an allowable error, a total concentration of the three types of amino acids can be measure by a single operation. Specifically, when a voltage is applied between the measuring electrode and the counter electrode during the measurement, in an analytical curve representing a relationship between an applied voltage and a current value for each of a plurality of specific amino acids, the applied voltage may include a voltage allowing the variety of the current values for the amino acids at the same applied voltage to fall within a given range. Preferably, the given range is set such that a ratio of a minimum value to a maximum value of currents in the three types of amino acids is about 80% or more, i.e., the variety of difference in current is about 20% or less of the maximum current value. If the variety of difference in currents falls within the above range, a total concentration of the three types of amino acids can be derived based on the currents with a maximum error of about 20% or less, i.e., with a practical degree of accuracy. More preferably, the applied voltage is set to allow the variety of current values for the three types of amino acids to be minimized.

Further, a plurality of enzymes different in substrate specificity and reaction rate are simultaneously used in different concentrations, and adjusted such that respective substrate specificities and reaction rates to the amino acids become equal to each other as a comprehensive reaction result of the enzymes, so that the variety of current values in the same concentration for the target amino acids can be narrowed. This makes it possible to measure a total concentration of a plurality of specific amino acids simultaneously in a simplified manner.

In a conventional method of determining an applied voltage at a measurement point, the measurement point is typically set at a point having a maximum current value. The method of the present invention is different from the conventional method in that an applied voltage at a measurement point is set at a voltage allowing a width of current output values for plural types of amino acids is minimized. This makes it possible to measure the plural types of amino acids by a single operation using an amino-acid biosensor having a single electrode system. In the determination of an applied voltage at a measurement point, with a view to increasing respective absolute current values for the plural types of amino acids while minimizing a spread (the variety) of the current values, the measurement point may be set at an intermediate value of the an applied voltage providing such characteristics. This makes it possible to reduce an error during measurement of the plural types of amino acids by a single operation, with enhanced measurement accuracy.

Figure 8:
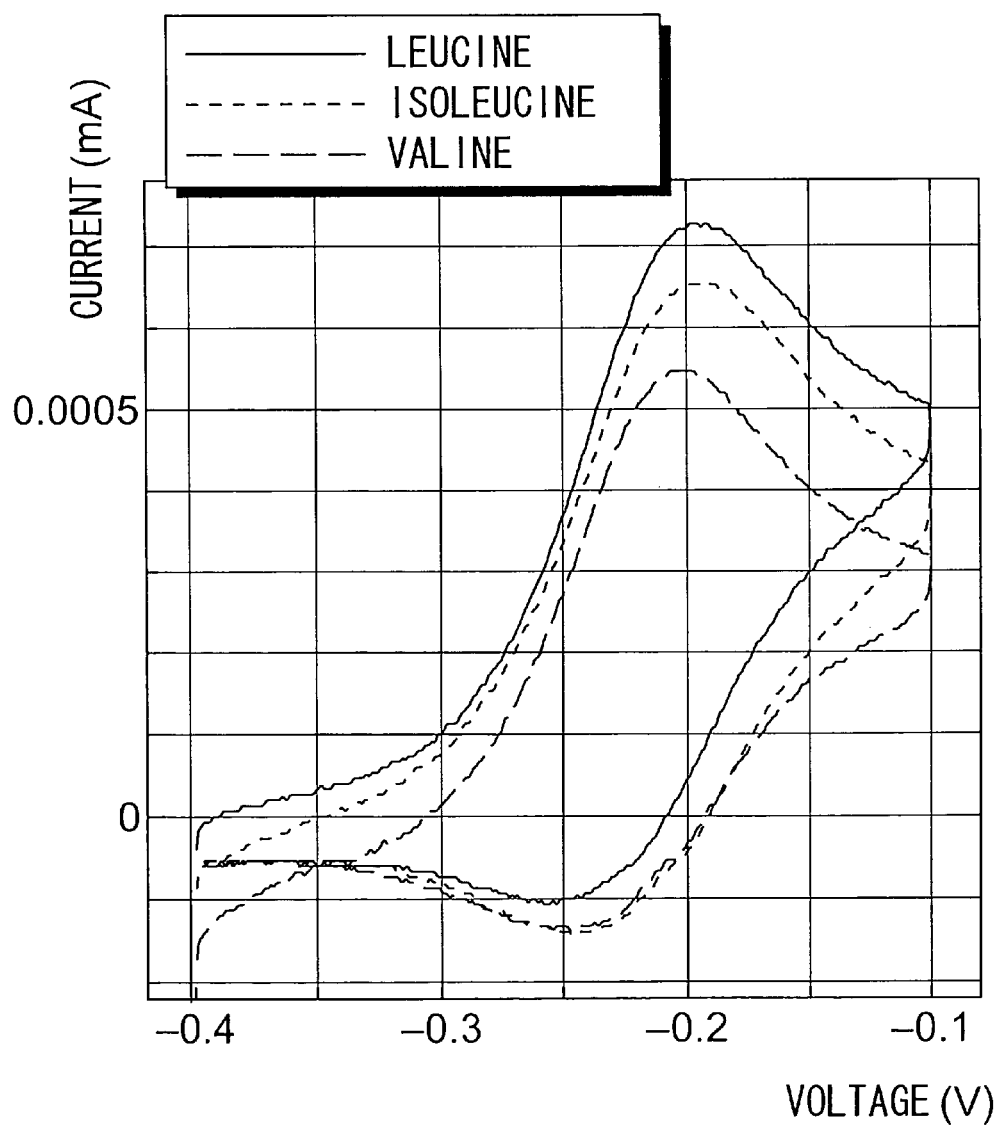
FIG. 8 is a graph showing an analytical curve representing voltage-current characteristics of three types of amino acids consisting of leucine, isoleucine and valine each having a concentration of 1 mM.

FIG. 8 is a graph showing analytical curves representing respective voltage-current characteristics of the three types of amino acids, or leucine, isoleucine and valine, in a concentration of 1 mM. Based on FIG. 8, a voltage providing a little variety of difference between current values for the three types of amino acids can be figured out. As seen in FIG. 8, while each of the graph curves of leucine, isoleucine and valine has approximately the same overall shape, a current value is generally the largest in the curve of leucine, and becomes lower in the curves of isoleucine and valine, in this order. A region having a small difference in absolute current value and a large absolute current value at a certain voltage corresponds to a region having a little variety of difference in current. As seen in FIG. 8, a difference in absolute current value becomes small in the voltage range of −0.275 V to −0.225 V. At a voltage of −0.225 V, i.e., at a point having the largest absolute current value in the above voltage range, a current in the curve of leucine exhibiting the largest current value is about 0.0006 mA, and a current in the curve of valine exhibiting the lowest current value is about 0.00048 mA. That is, a ratio of the current in valine to the current in leucine at this point is 0.00048/0.0006=80%, and therefore the variety of difference between current values of the three types of amino acids falls within 20% of the maximum current value. Thus, an applied voltage at the measurement point can be set at −0.225 V For comparison, at a voltage of −0.1 V, a current in the curve of leucine exhibiting the largest current value is about 0.00048 mA, and a current in the curve of valine exhibiting the lowest current value is about 0.0003 mA. That is, a ratio of the current in valine to the current in leucine at this point is 0.0003/0.00048=62.5%, and the variety of difference between current values of the three types of amino acids is increased to about 40% of the maximum current value. Thus, it is improper that an applied voltage at the measurement point is set at −0.1 V (Similarity in Amino-Acid Concentration-Current Characteristics of Branched-Chain Amino Acids)

Figure 9:
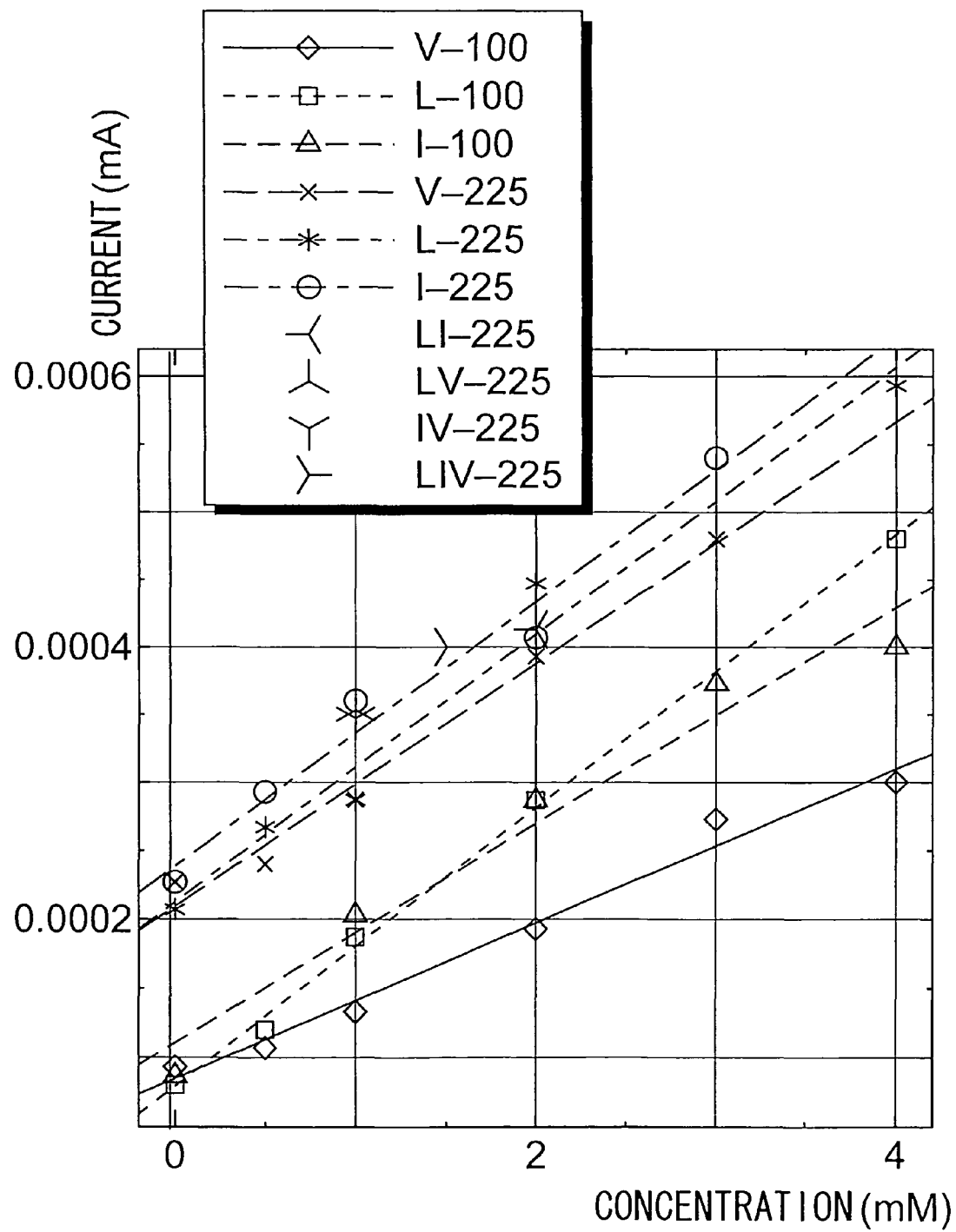
FIG. 9 is a graph showing an analytical curve representing amino-acid concentration-current characteristics of respective types of amino acids, wherein an applied voltage at a measurement point is used as a parameter.

FIG. 9 is a graph showing an analytical curve representing amino-acid concentration-current characteristics of respective types of amino acids, using an applied voltage at a measurement point as a parameter. Based on this graph, a relationship between an amino-acid concentration and a current in each of plural types of amino acids or mixtures thereof can be figured out. If the plural types of amino acids (or mixtures thereof) are similar to each other in a relationship between the amino-acid concentration and the current in under the condition that an applied voltage at a measurement point is kept at a constant value, the applied voltage allows these amino acids to be measured using an amino-acid biosensor having a single electrode system. In this graph, a symbol is plotted at each actually-measured point for each of the amino acids, and a linear approximate line is added to the actually-measured points for each of the amino acids. As to a mixture of a plurality of amino acids, actually-measured points are plotted. In the caption in FIG. 9, alphabetical letters V, L and I represent, respectively, valine, leucine and isoleucine, and a combination of the alphabetical letters represents a mixture of the corresponding amino acids. A numerical value attached to the end of each of the alphabetical letters indicates an applied voltage at a measurement point, and includes −100 mV and −225 mV. When the applied voltage is −100 mV, the graph curves of leucine and isoleucine are approximately similar to each other, but the graph line of valine is largely different from the graph lines of leucine and isoleucine. Comparing between them in terms of an inclination of each approximate line, an inclination of the line of valine is only ⅓ to ½ of those of other lines. Thus, the condition that the applied voltage is set at −100 mV is considered to be unsuitable for measuring the three types of branched-chain amino acids using an amino-acid biosensor having a single electrode system. When the applied voltage is −225 mV, the graph lines of the three types of branched-chain amino are highly similar to each other. Specifically, the lines of leucine and isoleucine have approximately the same inclination, and the line of isoleucine has a slightly larger current by about 0.025 μA. While the line of valine has a slightly smaller inclination than those of the lines of leucine and isoleucine, a current thereof in a concentration of about 0 mM is approximately equal to that in leucine. This shows that the three types of branched-chain amino acids can be measured using an amino-acid biosensor having a single electrode system. Further, a test was performed to verify that a concentration of a mixture of plural types of branched-chain amino acids is accurately measured under the condition that the applied voltage is set at −225 mV. Each line of a mixture of leucine and isoleucine (LI-225) having a concentration of 2 mM, a mixture of leucine and valine (LV-225) having a concentration of 1 mM, a mixture of isoleucine and valine (LIV-225) having a concentration of 1 mM and a mixture of leucine, isoleucine and valine (LIV-225) having a concentration of 1.5 mM, is similar to the respective approximate lines of the three types of branched-chain amino acids, and, in particular, highly similar to the respective approximate lines of leucine and isoleucine. This shows that, at an applied voltage of −225 mV under the above experimental conditions, a total concentration of the three types of branched-chain amino acids can be highly accurately measured using an amino-acid biosensor having a single electrode system. Thus, even in cases where various types of enzyme, coenzyme and mediator are selected to measure a total concentration of plural types of amino acids, an applied voltage can be optimally set in the same manner as that described above.

(Branched-Chain-Amino-Acid Biosensor)

Figure 10:
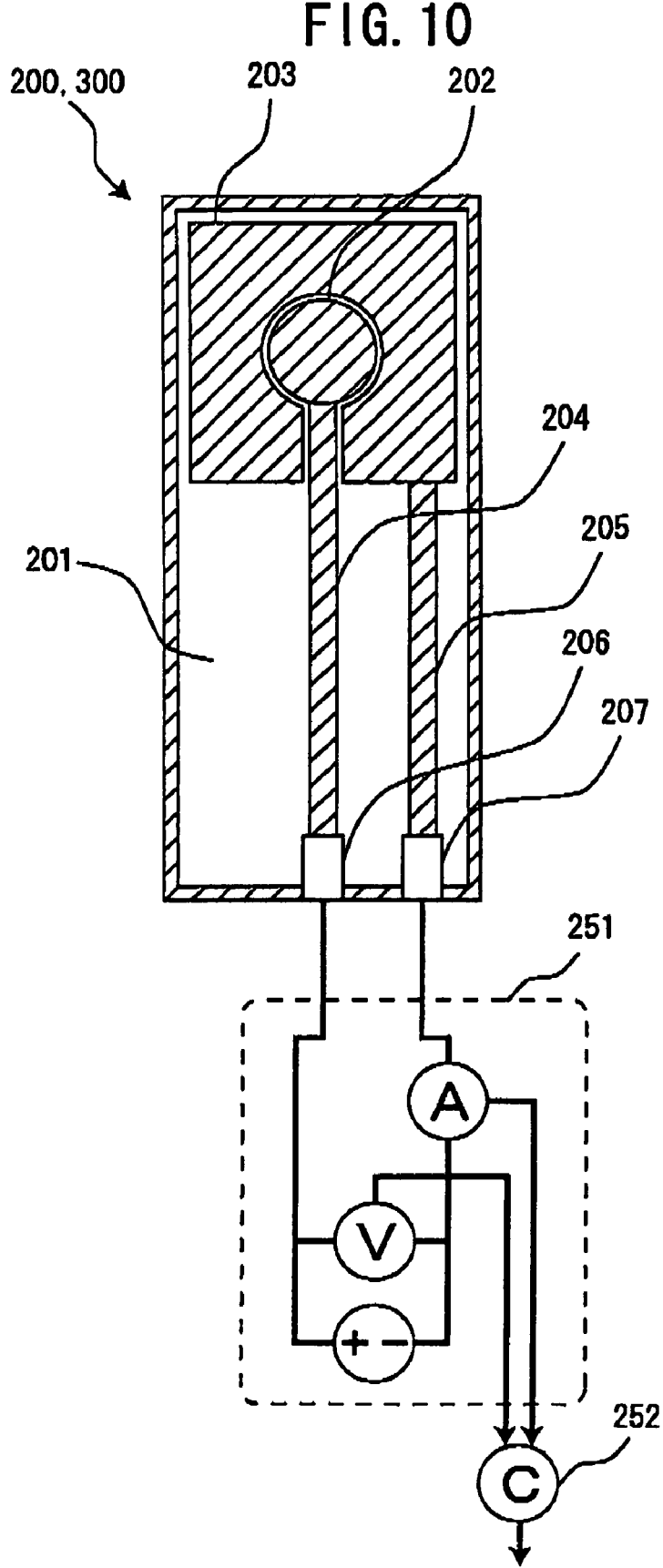
FIG. 10 is a schematic diagram showing the configuration of a branched-chain-amino-acid biosensor 200.

With reference to the drawing, the configuration of a branched-chain-amino-acid biosensor according to one embodiment of the present invention will be described. FIG. 10 is a schematic diagram showing the configuration of the branched-chain-amino-acid biosensor 200. In FIG. 10, the structure of a sensor section is illustrated in a top plan view, and the configuration of a circuit section is illustrated in a block diagram. The branched-chain-amino-acid biosensor 200 comprises a support member 201, a measuring electrode 202, a counter electrode 203, a measuring-electrode lead portion 204, a counter-electrode lead portion 205, a measuring-electrode terminal 206, a counter-electrode terminal 207, a voltage-current characteristic measurement section 251 and a concentration calculation section 252. The support member 201 is a base of the sensor section, and made, for example, of resin. The measuring electrode 202 is a electrode plate for allowing a reaction to be caused thereon so as to exchange electrons. The measuring electrode 202 has a surface on which an enzyme (leucine dehydrogenase), a coenzyme (NAD) and a mediator (PMS) are fixed. The enzyme, the coenzyme and the mediator are not necessarily fixed on the surface of the measuring electrode, but may be disposed in a reaction space formed between the electrodes of the electrode system by use of an absorbent support. In a measurement of a blood sample or the like, the sample is likely to contain a substance hindering an enzymatic reaction-based measurement. Thus, means for removing such a substance may be additionally provided. The measuring electrode 202 is equivalent to the working electrode 21. These elements may be fixed or immobilized using a conventional method. The measuring electrode 202 is connected to the measuring-electrode terminal 206 through the measuring-electrode lead portion 204. The counter electrode 203 is disposed in opposed relation to the measuring electrode 202, and adapted to allow a voltage to be applied between the measuring electrode 202 and counter electrode 203. Preferably, the counter electrode 203 has a shape surrounding the measuring electrode 202. The electrode system consisting of the measuring electrode 202 and the counter electrode 203 may be immersed in a sample solution 11. In the electrode system, a gap is formed between the measuring electrode 202 and the counter electrode 203 to allow the sample solution 11 to be held therein during measurement. The counter electrode 203 is connected to the counter-electrode terminal 207 through the counter-electrode lead portion 205. While this structure is a 2-electrode type, a 3-electrode type additionally having a reference electrode may be used. The voltage-current characteristic measurement section 251 is adapted to apply a voltage between the measuring electrode 206 and the counter electrode 207 during the measurement, and measure a resulting current. While the applied voltage for the measurement may be a fixed value or may be changed with time, it is necessary that, in an analytical curve representing a relationship between an applied voltage and a current value for each of the branched-chain amino acids, the applied voltage includes a voltage allowing the variety of the current values for the amino acids at the same applied voltage to fall within a given range. Based on a current measured at this applied voltage, a total concentration of the branched-chain amino acids can be accurately quantified. The concentration calculation section 252 is operable to receive the measured voltage-current characteristic from the voltage-current characteristic measurement section 251, and compare the received voltage-current characteristic with reference data on the analytical curve so as to calculate a branched-chain-amino-acid concentration. In a process of quantifying a branched-chain-amino-acid concentration from the current, the branched-chain-amino-acid concentration may be calculated based on an analytical curve prepared by additionally taking account of a relationship between the applied voltage and a time, to perform a more accurate measurement reflecting a temporal change. Further, a branched-chain-amino-acid concentration may be calculated in additional consideration of temperature by pre-measuring/pre-defining an analytical curve while additionally taking account of a temperature characteristic, and disposing a temperature sensor at a position adjacent to the electrode system so as to additionally measure a temperature.

An operation of the branched-chain-amino-acid biosensor 200 will be described below. Firstly, the electrode system applied with a voltage from the voltage-current characteristic measurement section 251 is immersed in the sample solution 11 containing the branched-chain amino acids to be measured. In a measurement of biological information, the sample solution 11 is a human-originated sample, such as blood. When the electrode system is immersed in the sample solution 11, each of leucine dehydrogenase, NAD and PMS fixed on the measuring electrode 202 are dissolved in the sample solution 11. The leucine dehydrogenase causes a dehydrogenation reaction in the branched-chain amino acids contained in the sample solution 11, and the NAD is changed to NADH during the reaction. The NADH gives electrons to the measuring electrode 202 through the PMS, and retunes to NAD due to oxidation. The measuring electrode 202 receives the electrons, and therefore a current flows from the counter electrode 203 to the measuring electrode 202. The voltage-current characteristic measurement section 251 measures a value of the current, and the concentration calculation section 252 receiving the measured current value calculates a branched-chain-amino-acid concentration. The calculated amino-acid concentration is output as data.

(Aromatic-Amino-Acid Biosensor)

Another embodiment of the present invention will be described below, wherein an amino acid to be measured is aromatic amino acids. Aromatic amino acids consisting of phenylalanine and tyrosine are structurally similar to each other in that they have a benzene ring in common, and thereby there is an enzyme having a substrate affinity to both of them. For example, phenylalanine dehydrogenase may be used for this purpose. A total concentration of aromatic amino acids can be measured using an amino-acid biosensor having a single electrode system by employing the above enzyme, and setting an applied voltage providing similar amino-acid concentration-current characteristics to the aromatic amino acids during measurement. That is, an aromatic-amino-acid biosensor 300 (not shown) can be prepared by, in the branched-chain-amino-acid biosensor 200, replacing the enzyme with the above enzyme, replacing the voltage-current characteristic measurement section 251 with a voltage-current characteristic measurement section adapted to provide a measurement point suitable for the aromatic amino acids, and replacing the concentration calculation section 252 with a concentration calculation section adapted to calculate an aromatic-amino-acid concentration. A coenzyme and a mediator may also be appropriately selected. The aromatic-amino-acid biosensor 300 operates in the same manner as that in the branched-chain-amino-acid biosensor 200.

(Fischer-ratio Biosensor)

Figure 11:
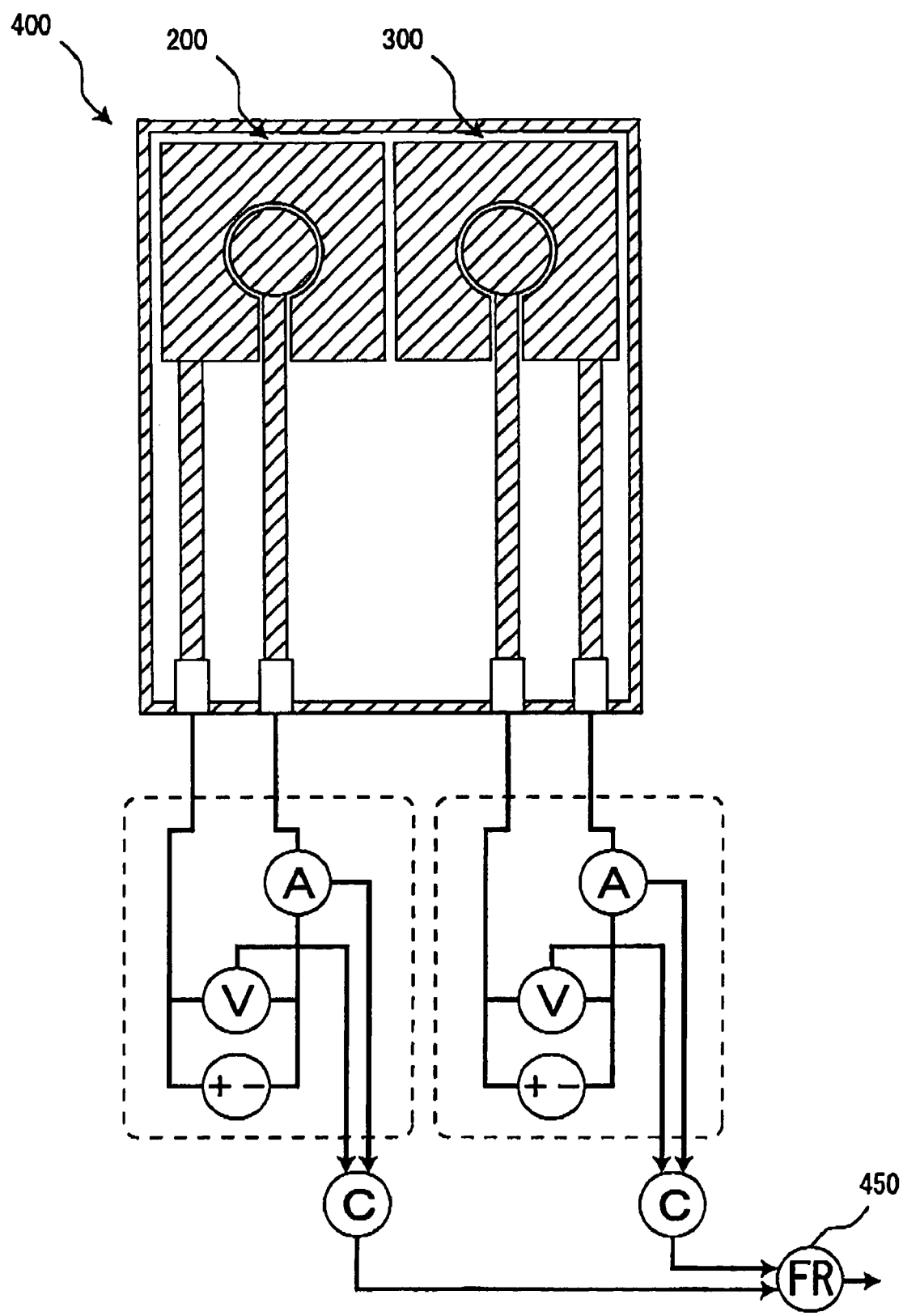
FIG. 11 is a schematic diagram showing the configuration of a Fischer-ratio biosensor 400.

A Fischer-ratio biosensor for measuring a Fischer ratio according to still another embodiment of the present invention will be described below. The Fischer-ratio biosensor 400 comprises a sensor section formed by combining the sensor section of the branched-chain-amino-acid biosensor 200 and a sensor section of the aromatic-amino-acid biosensor 300 together in such a manner that their electrode systems are disposed adjacent to each other. Based on this configuration, a branched-chain-amino-acid concentration and an amino-acid concentration in a sample solution 11 can be simultaneously measured. FIG. 11 is a schematic diagram showing the configuration of the Fischer-ratio biosensor 400. In FIG. 11, the structure of a sensor section is illustrated in a top plan view, and the configuration of a circuit section is illustrated in a block diagram. In FIG. 11, an element corresponding to the element of the branched-chain-amino-acid biosensor 200 in FIG. 10 is defined by the same reference numeral. The Fischer-ratio biosensor 400 comprises the branched-chain-amino-acid biosensor 200 and the aromatic-amino-acid biosensor 300 which have a common support member 201, and a Fischer-ratio calculation section 450. The Fischer-ratio calculation section 450 is operable to receive a branched-chain-amino-acid concentration and an amino-acid concentration, respectively, from two concentration measurement sections 252, 352, and dividing the branched-chain-amino-acid concentration by the amino-acid concentration to calculate a Fischer ratio. In a calculation of a BTR value, a tyrosine biosensor may be used in place of the aromatic-amino-acid biosensor. In this case, the enzyme includes tyrosine monooxygenase. The Fischer-ratio biosensor 400 can calculate a Fischer ratio by a single measurement operation. Further, the Fischer-ratio biosensor 400 can also output a branched-chain-amino-acid concentration and an amino-acid concentration independently.

(Other Biosensor)

In the above embodiments, biosensors for measuring a branched-chain-amino-acid concentration, an amino-acid concentration and a Fischer ratio have been described. The present invention can be extendingly applied to an amino-acid biosensor capable of measuring a total concentration of plural types of amino acid other than the above amino acids, using a single electrode system. Specifically, an enzyme, a coenzyme and a mediator may be selected in such a manner that, in an analytical curve representing a relationship between an applied voltage and a current value for each of the plural types of amino acids to be measured, they are operable, when a certain voltage is applied to an electrode system, to allow the variety of the current values for the amino acids at the same applied voltage to fall within a given range, and a measurement point may be selected to include the above applied voltage. Further, the present invention is not limited to amino-acid biosensors, but may be applied to a cholesterol biosensor and a hormone biosensor. Specifically, a biosensor capable of measuring plural types of substance other than amino acids using a single electrode system can be prepared by using an enzyme which has approximately the same substrate affinity to the plural types of substance. Further, a biosensor for measuring plural types of amino acids and a biosensor for measuring a single amino acid or a biological component may be combined together to form a single biosensor. That is, a biosensor may be configured to form two or more paths in a measurement circuit so as to simultaneously obtain a plurality of input values necessary for calculating an intended health index.

(Health Information Management System)

Each of the aforementioned branched-chain-amino-acid biosensor 200, aromatic-amino-acid biosensor 300 and Fischer-ratio biosensor 400 can measure a complex amino-acid diagnostic value, such as a Fischer ratio, by a single measurement operation in a simplified manner. Heretofore, such an amino-acid diagnostic value has been able to be measured only if a user transfers a biological sample, such as sampled blood, to a testing agency or the like, and therefore it has been necessary to take a long time before knowing a measurement result. Consequently, even though the diagnostic value, such as Fischer ratio, has a significantly important meaning in health, it has not been sufficiently utilized due to complexity of the measurement, until now. The biosensor of the present invention makes it possible to allow a hospital patient to take a diagnostic examination at bed side or allow a healthy person to measure a Fischer ratio or the like at his/her home in a simplified manner. This biosensor allowing a Fischer ratio or the like to be measured in a simplified manner on an individual basis makes it possible to establish a system for collecting a personally-measured Fischer ratio via a network, analyzing the Fischer ratio, and providing adequate health information about amino acids. A health information management system 500 according to one embodiment of the present invention is configured for the above purpose. This system 500 will be described below.

Figure 12:
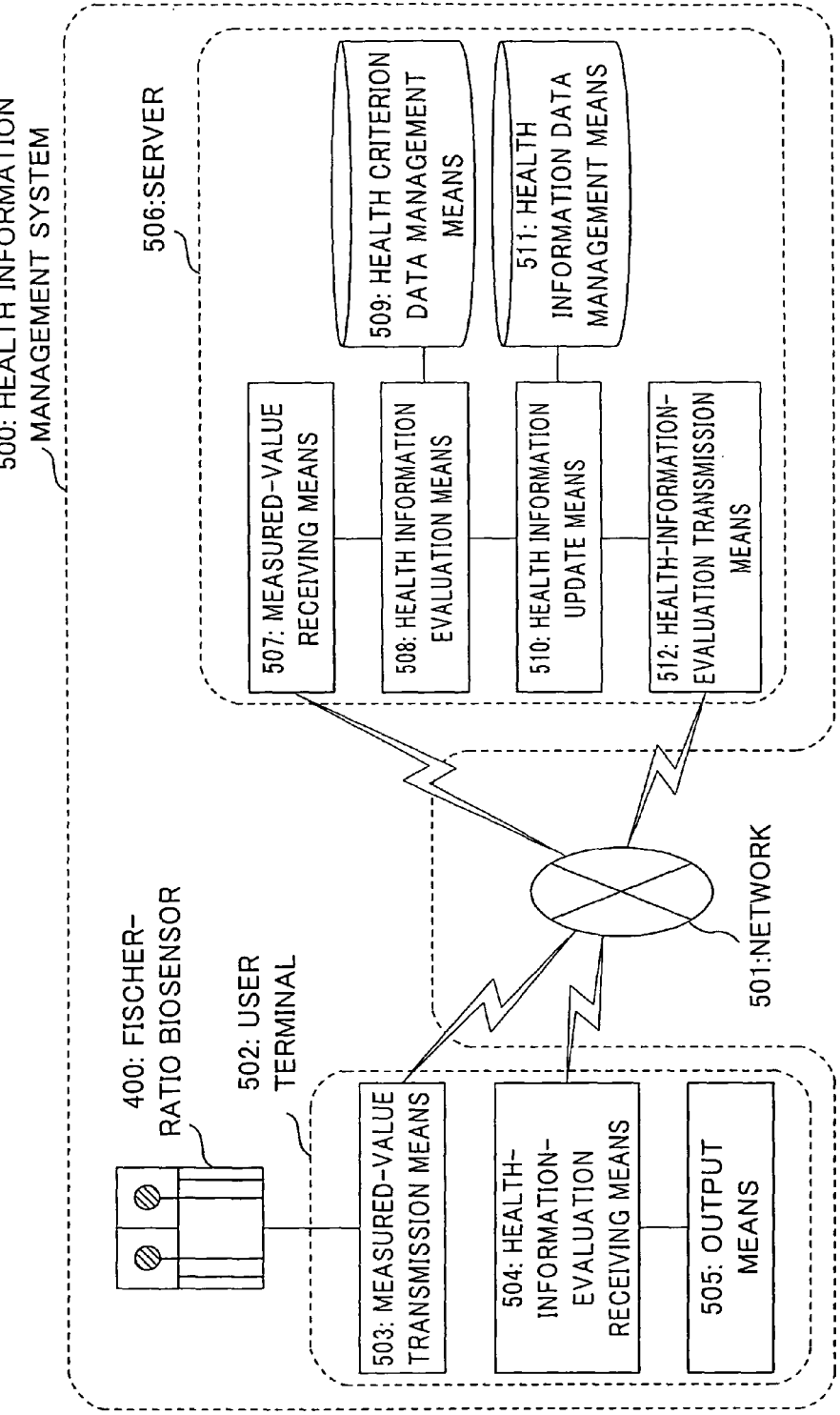
FIG. 12 is a schematic block diagram showing a health information management system 500.

With reference to FIG. 12, the configuration of the health information management system 500 according to one embodiment of the present invention will be described. FIG. 12 is a schematic block diagram showing the health information management system 500. The health information management system 500 generally comprises a Fischer-ratio biosensor 400, a user terminal 502 and a server 506. The Fischer-ratio biosensor 400 is connected to the user terminal 502, and operable to output a measured Fischer ratio to the user terminal 502. Preferably, the Fischer-ratio biosensor 400 is designed to output a branched-chain-amino-acid concentration and an aromatic-amino-acid concentration in addition to a Fischer ratio. The user terminal 502 is placed at user's home or the like to access the server 506 via a network 501. Preferably, the user terminal 502 is an information terminal, such as a personal computer (PC), a personal digital assistant (PDA), a telephone or a portable phone, which has a required application installed therein. Based on cooperation between the application and hardware, the user terminal 502 provides functional elements including Fischer-ratio transmission means 503, health-information-evaluation receiving means 504 and output means 505. The Fischer-ratio transmission means 503 is operable to transmit a measured value, such as a Fischer ratio, a branched-chain-amino-acid concentration and/or an aromatic-amino-acid concentration, received from the Fischer-ratio biosensor 400, to the server 506 via the network 501. The health-information-evaluation receiving means 504 is operable to receive a health information evaluation about the user's measured value, such as a Fischer ratio, from the server 6 via the network 501. The output means 505 is operable to output the received health information evaluation to a display screen or the like, and configured, for example, as a Web browser for outputting information through a display. The server 506 serves as a means to provide a health information management service. Typically, the server 506 is placed on the Web, and designed to provide the service through the Web. Based on cooperation between a health-information-management application and hardware, the server 506 provides functional elements including Fischer-ratio receiving means 507, health information evaluation means 508, health criterion data management means 509, health information update means 510, health information data management means 511 and health-information-evaluation transmission means 512. The Fischer-ratio receiving means 507 is operable to receive a measured value, such as a Fischer ratio, from the user terminal 502. The health information evaluation means 508 is operable to compare the received measured value, such as the received Fischer ratio, with criterion data stored in the health criterion data management means 509 so as to evaluate the measured value and derive a health information evaluation, such as an evaluation result and an associated comment. The health information update means 510 is operable to acquire a previous measured value of the user, such as a previous measured Fischer ratio, stored in the health information data management means 511 so as to update the previous measured value to a new measured value, and store the new measured value in the health information data management means 511. The health-information-evaluation transmission means 512 is operable to transmit the derived health information evaluation to the user terminal 502.

An operation of the health information management system 500 will be described below. Preferably, a user who intends to use the health information management system 500 registers as a membership in advance. For example, the registration may be performed through an Internet Web site. FIG. 13 is a schematic diagram showing a membership registration screen. Through this screen, membership's basic information is registered to the health information management system 500. The basic information to be registered includes name, sexuality, birth data, mail address, telephone number and e-mail address. In addition to the basic information, information about health, such as body height, body weight, blood type, personal medical history, level of alcohol drinking, smoking, diagnostic value about liver (GOT, GPT, γ-GTP, etc.), may be registered. This information may be supplementarily used for deriving health information. In response to the registration, a health information record for the membership is created and stored in the health information data management means 511.

Figure 15:
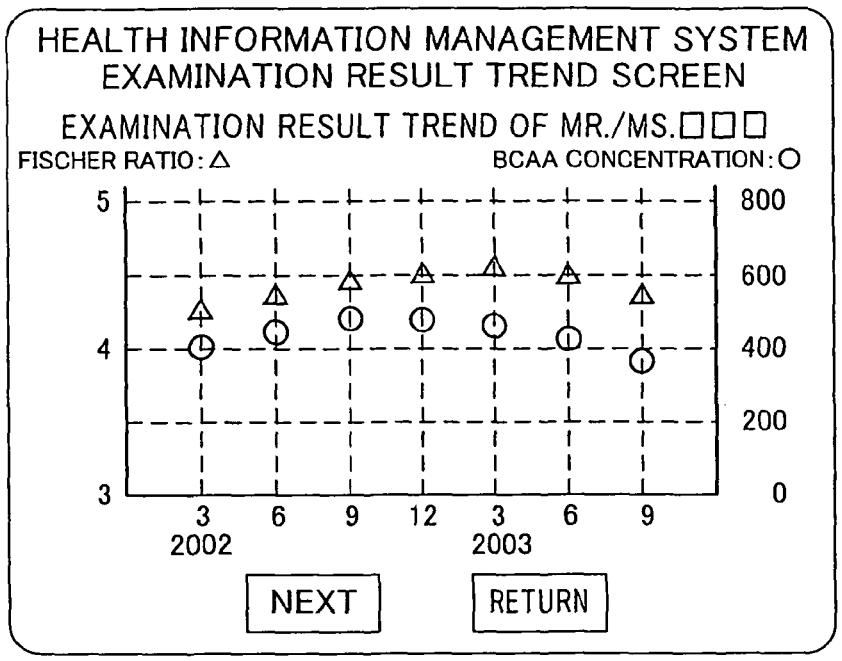
FIG. 15 is a schematic diagram showing a measured-value trend output screen for displaying a trend of measured values.
Figure 16:
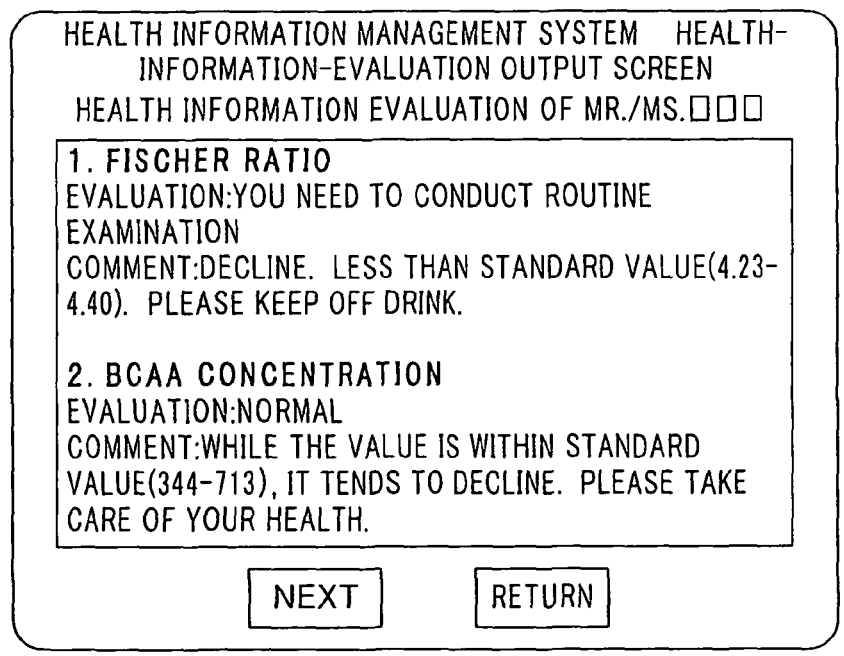
FIG. 16 is a schematic diagram showing a health-information-evaluation output screen for displaying a health-information evaluation.

The membership takes a small amount of tissue-fluid or blood sample by his/herself at home, and drops the sample onto a portion of the electrode system of the Fischer-ratio biosensor 400. Then, the Fischer-ratio biosensor 400 measures a Fischer ratio, a branched-chain-amino-acid concentration and an aromatic-amino-acid concentration of the blood sample, and outputs data of the measured values to the Fischer-ratio transmission means 503. The Fischer-ratio transmission means 503 transmits the measured values to the Fischer-ratio receiving means 507 via the network 501 together with information specifying the membership. Preferably, the user terminal 502 is operable, in response to receiving the measured values from the Fischer-ratio biosensor 400, to output/indicate the measured values from the output means 505. FIG. 14 is a schematic diagram showing a measured-value output screen for this purpose. The Fischer-ratio receiving means 507 sends the received measured values to the health information evaluation means 508. The health information evaluation means 508 acquires the standard or criterion values for a Fischer ratio and others, and compares the measured values with the corresponding criterion value to evaluate the measured values and extract a comment on the measured values so as to create a health information evaluation. Preferably, the criterion value is prepared on an age-by-age basis and on a sexuality-by-sexuality basis, and one of the criterion values corresponding to the age and sexuality of the membership is used. The health information update means 510 instructs the health information data management means 511 to retrieve previous health information of the membership so as to acquire the previous health information, and, after reflecting the new measured values thereto, store the updated health information in the health information data management means 511. The health information update means 510 also creates data representing a measured value trend. Preferably, the health information update means 510 forms a measured value trend graph. The health-information-evaluation transmission means 512 transmits the derived health information evaluation and the measured value trend graph to the user terminal 502 via the network 501. The health-information-evaluation receiving means 504 receives the health information evaluation and the measured value trend graph from the health-information-evaluation transmission means 512 via the network 501. The output means 505 indicates or displays the received measured value trend graph and health information evaluation. FIG. 15 is a schematic diagram showing a measured-value trend output screen for displaying the measured value trend. In the screen, the Fischer ratio and the branched-chain-amino-acid (BCAA) concentration are plotted in the form of a graph having a horizontal axis representing measurement data, i.e., indicated as a temporal trend. Preferably, symbols to be plotted are displayed with different colors depending on whether the measured value is within the criterion value or out of the criterion value, in a visually easily understood manner. FIG. 16 is a schematic diagram showing a health-information-evaluation output screen for displaying the health-information-evaluation. In the illustrated example, as to the measured Fischer ratio, an "Evaluation" field indicates "You need to conduct routine examination" because the measured value is less than the criterion value, and a "Comment" field indicates information to the effect that the value tends to decline and falls beyond the criterion value. As to the measured branched-chain-amino-acid concentration, an "Evaluation" field indicates "Normal" because the measured value is within the criterion value, and a "Comment" field indicates information to the effect that the value tends to decline. The "Comment" fields may be used for indicating information about a physical/health condition, information about a method for maintaining/improving a physical/health condition, information about diet menu, and/or information about contents/product of foods. As above, the health information management system 500 can measure/manage an amino acid-based value, such as a Fischer ratio, in a simplified manner, and provide health information about the measured value.

The biosensor of the present invention can be extendingly applied to measurements of various types of amino acids and biological components. Thus, a health information management system using such biosensors may also be applied to a biological information management system having little direct relation to health. That is, as used in the specification, the term "health information" may include any biological information including information about an index which has not been recognized that it has direct relationship with health.

What is claimed is:

1. An amino-acid biosensor for measuring a total concentration of a plurality of specific amino acids, comprising
a measuring electrode which includes as components a mediator and an enzyme which selectively act on at least said plurality of specific amino acids each serving as a substrate, a counter electrode, and a voltage-current characteristic measurement section, said measuring electrode and said counter electrode being connected to said voltage-current characteristic measurement section to apply a voltage therebetween, wherein:

said enzyme has a substrate affinity to each of said plurality of specific amino acids;

said enzyme is operable to catalyze a reaction in each of said plurality of specific amino acids as a substrate so as to form a reaction product;

said mediator is operable, during amino-acid concentration measurement, to carry electrons between said reaction product and said measuring electrode, and said voltage-current characteristic measurement section applies a voltage between said measuring electrode and said counter electrode during the measurement, which applied voltage includes a voltage that allows a variety of current values for said plurality of specific amino acids at a same concentration and a same applied voltage to fall within about 20% or less of a maximum of said current values at said applied voltage in an analytical curve representing a relationship between said applied voltage and said respective current value at a specific concentration for each of said plurality of specific amino acids, whereby said total concentration of said plurality of specific amino acids is measured by said biosensor.

2. The amino-acid biosensor as defined in claim 1, wherein:
said measuring electrode further includes a coenzyme as a component;

said enzyme consists of a dehydrogenase;

said reaction product consists of a reduced coenzyme derived by reduction of said coenzyme; and said mediator is operable, during the amino-acid concentration measurement, to carry electrons from said reduced coenzyme to said measuring electrode.

3. A branched-chain-amino-acid biosensor comprising the amino-acid biosensor as defined in claim 2, wherein:
said plurality of specific amino acids consists of branched-chain amino acids including leucine, valine and isoleucine;

said dehydrogenase consists of leucine dehydrogenase; and said coenzyme consists of nicotinamide adenine dinucleotide.

4. The branched-chain-amino-acid biosensor as defined in claim 3, wherein said mediator consists of 1-methoxy-5-methyl-phenazinium methyl sulfate (PMS).

5. An aromatic-amino-acid biosensor comprising the amino-acid biosensor as defined in claim 2, wherein:
said plurality of specific amino acids consist of aromatic amino acids including phenylalanine and tyrosine; and said dehydrogenase consists of phenylalanine dehydrogenase.

6. A Fischer-ratio biosensor, comprising:
a branched-chain-amino-acid biosensor and an aromatic-amino-acid biosensor each comprising the amino-acid biosensor as defined in claim 2, wherein for the branched-chain-amino-acid biosensor:

said plurality of specific amino acids consists of branched-chain amino acids including leucine, valine and isoleucine;

said dehydrogenase consists of leucine dehydrogenase; and said coenzyme consists of nicotinamide adenine dinucleotide, and wherein for the aromatic-amino-acid biosensor:

said plurality of specific amino acids consist of aromatic amino acids including phenylalanine and tyrosine; and said dehydrogenase consists of phenylalanine dehydrogenase; and Fischer-ratio calculation means for dividing a branched-chain-amino-acid concentration measured using said branched-chain-amino-acid biosensor by an aromatic-amino-acid concentration measured using said aromatic-amino-acid biosensor, to calculate a Fischer ratio.

* * * * *